US012606525B2

(12) United States Patent
Perni et al.

(10) Patent No.: US 12,606,525 B2
(45) Date of Patent: *Apr. 21, 2026

(54) DIMETHYLTRYPTAMINE ANALOGUES AS NITRIC OXIDE DELIVERY DRUGS

(71) Applicant: ATAI Therapeutics, Inc., New York, NY (US)

(72) Inventors: Robert B. Perni, Marlborough, MA (US); Glenn Short, Scituate, MA (US); Tanweer A. Khan, Berlin (DE)

(73) Assignee: Atai Therapeutics, Inc., New York, NY (US)

( * ) Notice: Subject to any disclaimer, the term of this patent is extended or adjusted under 35 U.S.C. 154(b) by 50 days.

This patent is subject to a terminal disclaimer.

(21) Appl. No.: 18/657,306

(22) Filed: May 7, 2024

(65) Prior Publication Data

US 2024/0400511 A1 Dec. 5, 2024

Related U.S. Application Data

(63) Continuation of application No. 18/147,499, filed on Dec. 28, 2022, now Pat. No. 12,012,381.

(60) Provisional application No. 63/295,199, filed on Dec. 30, 2021.

(51) Int. Cl.
*C07D 209/16* (2006.01)

(52) U.S. Cl.
CPC ........ *C07D 209/16* (2013.01); *C07B 2200/05* (2013.01)

(58) Field of Classification Search
CPC .................................................... C07D 209/16
See application file for complete search history.

(56) References Cited

U.S. PATENT DOCUMENTS

| | | | |
|---|---|---|---|
| 860,913 | A | 7/1907 | Haeberlein |
| 3,499,003 | A | 3/1970 | Welstead, Jr. |
| 3,594,391 | A | 7/1971 | Wolf et al. |
| 3,781,300 | A | 12/1973 | Wolf et al. |
| 4,252,803 | A | 2/1981 | Webb |
| 5,340,838 | A | 8/1994 | Gidda et al. |
| 5,347,029 | A | 9/1994 | Johnson |
| 5,637,593 | A | 6/1997 | Porter et al. |
| 5,705,527 | A | 1/1998 | Ishihara et al. |
| 6,201,025 | B1 | 3/2001 | Dax et al. |
| 6,403,808 | B1 | 6/2002 | Glennon et al. |
| 6,436,950 | B1 | 8/2002 | Achari et al. |
| 6,500,456 | B1 | 12/2002 | Capella |
| 8,268,856 | B2 | 9/2012 | Hamann et al. |
| 9,388,395 | B2 | 7/2016 | Nazor et al. |
| 9,549,942 | B2 | 1/2017 | Jo et al. |
| 9,720,005 | B2 | 8/2017 | McConnell et al. |
| 10,064,856 | B2 | 9/2018 | Bosse et al. |
| 10,550,140 | B2 | 2/2020 | Wiles et al. |
| 11,242,318 | B2 | 2/2022 | Nivorozhkin et al. |
| 11,292,765 | B2 | 4/2022 | Bryson |
| 11,332,441 | B2 | 5/2022 | Chadeayne |
| 11,406,619 | B2 | 8/2022 | Layzell et al. |
| 11,478,449 | B1 | 10/2022 | Witowski et al. |
| 11,591,353 | B2 | 2/2023 | Slassi et al. |
| 11,602,521 | B2 | 3/2023 | Rao et al. |
| 11,643,391 | B2 | 5/2023 | Perni et al. |
| 11,759,452 | B2 | 9/2023 | Witowski et al. |
| 12,012,381 | B2 | 6/2024 | Perni et al. |
| 12,053,453 | B2 | 8/2024 | Witowski et al. |

(Continued)

FOREIGN PATENT DOCUMENTS

| | | |
|---|---|---|
| EP | 0821957 A2 | 2/1998 |
| EP | 1336602 A1 | 8/2003 |

(Continued)

OTHER PUBLICATIONS

Abiero et al., "Four Novel Synthetic Tryptamine Analogs Induce Head-Twitch Responses and Increase 5-HTR2a in the Prefrontal Cortex in Mice", Biomol Ther (Seoul). Jan. 1, 2020; 28(1): 83-91.
Andersson et al., "Psychoactive substances as a last resort—a qualitative study of self-treatment of migraine and cluster headaches", Harm Reduction Journal, Dec. 2017, 10 pages.
Archer et al., "5-Methoxy-N, N-dimethyltryptamine-induced analgesia is blocked by alpha-adrenoceptor antagonists in rats", British J. Pharmac., Oct. 1986, pp. 293-298.
Baker et al., "Neurochemical and neuropharmacological investigation of N-cyanoethyltryptamine, a potential prodrug of tryptamine", Proc West Pharmacol Soc., 1987; 30: 307-11.
Banker, G. S., et al., "Prodrugs", Modern Pharmaceutics, Third Edition, Revised, and Expanded, Marcel Dekker, Inc. (1996); pp. 451 and 596; 3 pages.

(Continued)

*Primary Examiner* — Daniel R Carcanague
(74) *Attorney, Agent, or Firm* — COOLEY LLP

(57) ABSTRACT

Provided herein are compounds of Formula (I), (II), or a pharmaceutically acceptable salt thereof. Also provided herein are pharmaceutical compositions comprising a compound of Formula (I), (II), or pharmaceutically acceptable salt thereof, and methods of using a compound of Formula (I), (II), or a pharmaceutically acceptable salt thereof.

(I)

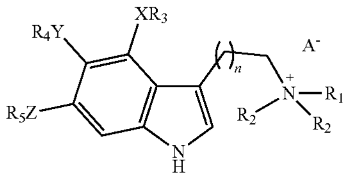

(II)

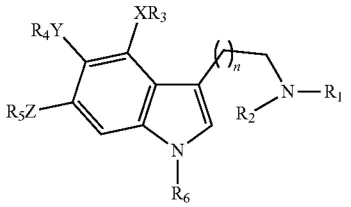

34 Claims, No Drawings

(56) References Cited

U.S. PATENT DOCUMENTS

| | | | |
|---|---|---|---|
| 12,065,405 | B2 | 8/2024 | Perni |
| 12,128,027 | B2 | 10/2024 | Rao et al. |
| 12,378,194 | B2 | 8/2025 | Short et al. |
| 12,396,982 | B2 | 8/2025 | Witowski et al. |
| 12,472,163 | B2 | 11/2025 | Witowski et al. |
| 2002/0052370 | A1 | 5/2002 | Barber et al. |
| 2002/0115715 | A1 | 8/2002 | Dax et al. |
| 2003/0079301 | A1 | 5/2003 | Sauter et al. |
| 2004/0235899 | A1 | 11/2004 | Maria Assunta et al. |
| 2005/0152858 | A1 | 7/2005 | Bertz et al. |
| 2005/0245594 | A1 | 11/2005 | Sutter et al. |
| 2005/0250839 | A1 | 11/2005 | Marnett et al. |
| 2007/0099909 | A1 | 5/2007 | Chen et al. |
| 2007/0140977 | A1 | 6/2007 | Yoneto et al. |
| 2008/0248511 | A1 | 10/2008 | Daily et al. |
| 2008/0306025 | A1 | 12/2008 | Yu et al. |
| 2008/0318957 | A1 | 12/2008 | Glinka et al. |
| 2009/0221549 | A1 | 9/2009 | Gerber et al. |
| 2010/0113539 | A1 | 5/2010 | Scott et al. |
| 2010/0166889 | A1 | 7/2010 | Sanfilippo |
| 2011/0245215 | A1 | 10/2011 | Carrara et al. |
| 2012/0028995 | A1 | 2/2012 | Ansorge et al. |
| 2012/0108510 | A1 | 5/2012 | Young et al. |
| 2012/0122948 | A1 | 5/2012 | Soubhye et al. |
| 2015/0071994 | A1 | 3/2015 | Schentag et al. |
| 2015/0284365 | A1 | 10/2015 | Elder et al. |
| 2015/0346226 | A1 | 12/2015 | Mcconnell et al. |
| 2016/0002195 | A1 | 1/2016 | Makriyannis et al. |
| 2016/0074411 | A1 | 3/2016 | Krumpl |
| 2016/0106694 | A1 | 4/2016 | Roberts et al. |
| 2016/0303079 | A1 | 10/2016 | Hung |
| 2018/0221396 | A1 | 8/2018 | Chadeayne |
| 2019/0315689 | A1 | 10/2019 | Chen et al. |
| 2019/0345103 | A1 | 11/2019 | Batchelor et al. |
| 2020/0199119 | A1 | 6/2020 | Thompson et al. |
| 2020/0325124 | A1 | 10/2020 | Lavoie et al. |
| 2020/0390746 | A1 | 12/2020 | Rands et al. |
| 2020/0397752 | A1 | 12/2020 | Perez Castillo et al. |
| 2021/0015738 | A1 | 1/2021 | LaRosa et al. |
| 2021/0085671 | A1 | 3/2021 | Chadeayne |
| 2021/0108238 | A1 | 4/2021 | Protzko |
| 2021/0145851 | A1 | 5/2021 | Stamets |
| 2021/0236523 | A1 | 8/2021 | Schindler et al. |
| 2021/0277433 | A1 | 9/2021 | Protzko |
| 2021/0292278 | A1 | 9/2021 | Chadeayne |
| 2021/0322306 | A1 | 10/2021 | Espinoza et al. |
| 2021/0322447 | A1 | 10/2021 | Plakogiannis et al. |
| 2021/0346347 | A1 | 11/2021 | Witowski et al. |
| 2021/0353615 | A1 | 11/2021 | Chadeayne |
| 2021/0363104 | A1 | 11/2021 | Nivorozhkin et al. |
| 2021/0378969 | A1 | 12/2021 | Rands et al. |
| 2021/0395201 | A1 | 12/2021 | Rands et al. |
| 2021/0403425 | A1 | 12/2021 | Bryson |
| 2022/0015749 | A1 | 1/2022 | Sanders et al. |
| 2022/0024956 | A1 | 1/2022 | Slassi et al. |
| 2022/0031662 | A1 | 2/2022 | Terwey |
| 2022/0071958 | A1 | 3/2022 | Terwey |
| 2022/0079881 | A1 | 3/2022 | Modi |
| 2022/0096504 | A1 | 3/2022 | Blumstock et al. |
| 2022/0259147 | A1 | 8/2022 | Feilding-Mellen |
| 2022/0267267 | A1 | 8/2022 | Feilding-Mellen |
| 2022/0273628 | A1 | 9/2022 | Liechti et al. |
| 2022/0304980 | A1 | 9/2022 | Arnold et al. |
| 2022/0339139 | A1 | 10/2022 | Rao et al. |
| 2022/0354824 | A1 | 11/2022 | Witowski et al. |
| 2022/0388956 | A1 | 12/2022 | Fawaz |
| 2023/0041584 | A1 | 2/2023 | Perni et al. |
| 2023/0066720 | A1 | 3/2023 | Perni et al. |
| 2023/0099972 | A1 | 3/2023 | Rao et al. |
| 2023/0136824 | A1 | 5/2023 | Rao et al. |
| 2023/0227407 | A1 | 7/2023 | Perni et al. |
| 2023/0227421 | A1 | 7/2023 | Perni et al. |
| 2023/0233537 | A1 | 7/2023 | Dornbierer et al. |
| 2023/0310374 | A1 | 10/2023 | Rao et al. |
| 2023/0321039 | A1 | 10/2023 | Rao et al. |
| 2023/0322735 | A1 | 10/2023 | Kruegel |
| 2023/0357146 | A1 | 11/2023 | Perni et al. |
| 2023/0372295 | A1 | 11/2023 | Witowski et al. |
| 2024/0116896 | A1 | 4/2024 | Khan et al. |
| 2024/0199544 | A1 | 6/2024 | Fawaz et al. |
| 2024/0287107 | A1 | 8/2024 | Khan |
| 2024/0307350 | A1 | 9/2024 | Terwey |
| 2024/0415811 | A1 | 12/2024 | Gray |
| 2025/0002457 | A1 | 1/2025 | Yacoub et al. |
| 2025/0041273 | A1 | 2/2025 | Witowski et al. |
| 2025/0064783 | A1 | 2/2025 | Witowski et al. |
| 2025/0163044 | A1 | 5/2025 | Banister et al. |
| 2025/0235428 | A1 | 7/2025 | Witowski et al. |

FOREIGN PATENT DOCUMENTS

| | | | | | |
|---|---|---|---|---|---|
| WO | WO-9323364 | A1 | | 11/1993 | |
| WO | WO-9506638 | A1 | | 3/1995 | |
| WO | WO-9524200 | A1 | | 9/1995 | |
| WO | WO-9617842 | A1 | | 6/1996 | |
| WO | WO-0041755 | A1 | | 7/2000 | |
| WO | WO-0051672 | A1 | | 9/2000 | |
| WO | WO-0211800 | A2 | | 2/2002 | |
| WO | WO-02068029 | A2 | | 9/2002 | |
| WO | WO-02068030 | A2 | | 9/2002 | |
| WO | WO-02068031 | A2 | | 9/2002 | |
| WO | WO-02068032 | A2 | | 9/2002 | |
| WO | WO-03000310 | A2 | | 1/2003 | |
| WO | WO-03020350 | A1 | | 3/2003 | |
| WO | WO-03026559 | A2 | | 4/2003 | |
| WO | WO-03082393 | A1 | | 10/2003 | |
| WO | WO-03084591 | A1 | | 10/2003 | |
| WO | WO-03090812 | A2 | | 11/2003 | |
| WO | WO-2004043462 | A1 | | 5/2004 | |
| WO | WO-2006099416 | A1 | | 9/2006 | |
| WO | WO-2006105615 | A1 | | 10/2006 | |
| WO | WO-2010151258 | A1 | | 12/2010 | |
| WO | WO-2011041870 | A1 | | 4/2011 | |
| WO | WO-2013063492 | A1 | | 5/2013 | |
| WO | WO-2018064465 | A1 | | 4/2018 | |
| WO | WO-2018081456 | A1 | | 5/2018 | |
| WO | WO-2018094106 | A2 | | 5/2018 | |
| WO | WO-2018148605 | A1 | | 8/2018 | |
| WO | WO-2018195455 | A1 | | 10/2018 | |
| WO | WO-2019064031 | A1 | | 4/2019 | |
| WO | WO-2019081764 | A1 | | 5/2019 | |
| WO | WO-2019213551 | A1 | | 11/2019 | |
| WO | WO-2020037372 | A1 | | 2/2020 | |
| WO | WO-2020157569 | A1 | | 8/2020 | |
| WO | WO-2020169850 | A1 | | 8/2020 | |
| WO | WO-2020169851 | A1 | | 8/2020 | |
| WO | WO-2020176597 | A1 | | 9/2020 | |
| WO | WO-2020181194 | A1 | | 9/2020 | |
| WO | WO-2020212951 | A1 | | 10/2020 | |
| WO | WO-2021003467 | A1 | | 1/2021 | |
| WO | WO-2021041407 | A1 | * | 3/2021 | ........... C07D 209/16 |
| WO | WO-2021155468 | A1 | | 8/2021 | |
| WO | WO-2021168082 | A1 | | 8/2021 | |
| WO | WO-2021188782 | A1 | | 9/2021 | |
| WO | WO-2021226041 | A1 | | 11/2021 | |
| WO | WO-2021226416 | A1 | | 11/2021 | |
| WO | WO-2021244831 | A1 | | 12/2021 | |
| WO | WO-2021250434 | A1 | | 12/2021 | |
| WO | WO-2021250435 | A1 | | 12/2021 | |
| WO | WO-2021259962 | A1 | | 12/2021 | |
| WO | WO-2022051670 | A1 | | 3/2022 | |
| WO | WO-2022061242 | A1 | | 3/2022 | |
| WO | WO-2022082058 | A1 | | 4/2022 | |
| WO | WO-2022109050 | A1 | | 5/2022 | |
| WO | WO-2022123232 | A1 | | 6/2022 | |
| WO | WO-2022150675 | A1 | | 7/2022 | |
| WO | WO-2022160056 | A1 | | 8/2022 | |
| WO | WO-2022170442 | A1 | | 8/2022 | |
| WO | WO-2022195011 | A1 | | 9/2022 | |
| WO | WO-2022232179 | A1 | | 11/2022 | |
| WO | WO-2022235514 | A1 | | 11/2022 | |
| WO | WO-2022235529 | A1 | | 11/2022 | |
| WO | WO-2022243285 | A1 | | 11/2022 | |
| WO | WO-2022246572 | A1 | | 12/2022 | |

(56) References Cited

FOREIGN PATENT DOCUMENTS

| | | | |
|---|---|---|---|
| WO | WO-2022251351 | A1 | 12/2022 |
| WO | WO-2022261383 | A1 | 12/2022 |
| WO | WO-2023283386 | A2 | 1/2023 |
| WO | WO-2023021112 | A1 | 2/2023 |
| WO | WO-2023036473 | A1 | 3/2023 |
| WO | WO-2023055992 | A1 | 4/2023 |
| WO | WO-2023076135 | A1 | 5/2023 |
| WO | WO-2023076150 | A1 | 5/2023 |
| WO | WO-2023078604 | A1 | 5/2023 |
| WO | WO-2023111544 | A2 | 6/2023 |
| WO | WO-2023115166 | A1 | 6/2023 |
| WO | WO-2023129956 | | 7/2023 |
| WO | WO-2024054866 | A2 | 3/2024 |
| WO | WO-2024092106 | A2 | 5/2024 |
| WO | WO-2024118767 | A2 | 6/2024 |
| WO | WO-2024119075 | A1 | 6/2024 |
| WO | WO-2024130140 | A2 | 6/2024 |
| WO | WO-2024130140 | A3 | 7/2024 |
| WO | WO-2024227149 | A2 | 10/2024 |
| WO | WO-2024243488 | A2 | 11/2024 |
| WO | WO-2025019800 | A1 | 1/2025 |
| WO | WO-2025024637 | A1 | 1/2025 |
| WO | WO-2025054397 | A1 | 3/2025 |
| WO | WO-2025076151 | A1 | 4/2025 |
| WO | WO-2025137581 | A1 | 6/2025 |
| WO | WO-2025170990 | A1 | 8/2025 |

OTHER PUBLICATIONS

Barker, “Administration of N, N-dimethyltryptamine (DMT) in psychedelic therapeutics and research and the study of endogenous DMT”, Psychopharmacology (Berl). Jun. 2022; 239(6): 1749-1763. Epub Jan. 22, 2022, with erratum, 16 pages.

Barker, “N, N-Dimethyltryptamine (DMT), an Endogenous Hallucinogen: Past, Present, and Future Research to Determine Its Role and Function.” Front Neurosci. Aug. 6, 2018:12:536. doi: 10.3389/fnins.2018.00536. eCollection 2018. 17 pages.

Barsuglia et al., “Intensity of mystical experiences occasioned by 5-MeO-DMT and comparison with a prior psilocybin study,” Front. Psychol., Dec. 2018, 6 pages.

Benneyworth et al., “Complex discriminative stimulus properties of (+)lysergic acid diethylamide (LSD) in C57Bl/6J mice.” Psychopharmacology (2005) 179, 854-862.

Berge et al., “Pharmaceutical salts”, Journal of Pharmaceutical Sciences (Jan. 1977); 66(1): 1-19.

Bergin, “Preliminary X-ray crystallographic study of some psychoactive indole bases.” Acta Cryst. (1968). B24, 882, https://doi.org/10.1107/S0567740868003353, 1 page.

Bergin, “The structure of the catecholamines. II. The crystal structure of dopamine hydrochloride.” Acta Crystallogr B Struct Crystallogr Cryst Chem. Nov. 15, 1968;24(11):1506-10. doi: 10.1107/s0567740868004553.

Bibi et al., “Use of Permeapad® for prediction of buccal absorption: A comparison to in vitro, ex vivo and in vivo method,” Eur J Pharm Sci. Oct. 10, 2016:93:399-404. doi:10.1016/j.ejps.2016.08.041. Epub Aug. 24, 2016.

Blough, B. E., et al., “Alpha-ethyltryptamines as dual dopamine-serotonin releasers”, Bioorganic & Medicinal Chemistry Letters (2014); 24(19): 4754-4758. doi: 10.1016/j.bmcl.2014.07.062. Epub Jul. 29, 2014.

Brandt et al., “Analytical methods for psychoactive N, N-dialkylated tryptamines”, Trends in Analytical Chemistry, vol. 29, No. 8, 2010, pp. 858-869.

Brandt et al., “Characterization of the synthesis of N,N-dimethyltryptamine by reductive amination using gas chromatography ion trap mass spectrometry.” Drug Test Anal 2(7):330-338 (2010).

Brito-Da-Costa, et al., “Toxicokinetics and toxicodynamics of ayahuasca alkaloids N, N-dimethyltryptamine (DMT), harmine, harmaline and tetrahydroharmine: clinical and forensic impact”, Pharmaceuticals, Oct. 2020, 36 pages.

Buchwald, Peter, “Soft drugs: design principles, success stories, and future perspectives”, Expert Opin Drug Metab Toxicol. Aug. 2020; 16(8): 645-650. Epub Jun. 20, 2020.

Bugaenko et al., “Synthesis of indoles: recent advances”, Russ. Chem. Rev., 2019, 88 (2)99-159, 62 pages.

Cameron, Lindsay, P. et al., “Chronic, Intermittent Microdoses of the Psychedelic N , N-Dimethyltryptamine (DMT) Produce Positive Effects on Mood and Anxiety in Rodents”, ACS Chemical Neuroscience, vol. 10, No. 7, Jul. 17, 2019 (Jul. 17, 2019), pp. 3261-3270.

Cameron, L.P., et al.; “A non-hallucinogenic psychedelic analogue with therapeutic potential,” Nature; 589(7842):474-479 (2021).

Cameron P L et al., “Effects of N, N-Dimethyltryptamine on Rat Behaviors Relevant to Anxiety and Depression”, ACS Chem. Neuroscience, 2018, pp. 1582-1590.

Carhart-Harris et al., “The therapeutic potential of psychedelic drugs: past, present, and future”, Neuropsychopharmacology (2017); 42(11): 2105-2113. doi: 10.1038/npp.2017.84. Epub Apr. 26, 2017.

Carhart-Harris, “Psilocybin for treatment-resistant depression: fMRI-measured brain mechanisms.” Sci Rep. Oct. 13, 2017; 7(1): 13187. doi: 10.1038/s41598-017-13282-7. 11 pages.

Carter et al., “Modulating the rate and rhythmicity of perceptual rivalry alternations with the mixed 5-HT2A and 5-HT1A agonist psilocybin”, Neuropsychopharmacology (2005); 30(6): 1154-1162. doi: 10.1038/sj.npp.1300621.

Carvalho et al., “Mucoadhesive drug delivery systems,” BJPS, vol. 46, n. 1, Jan./Mar. 2010. 18 pages.

CAS Registry No. 1152718-19-8, Benzenemethanamine, N-[4-(1,1-dimethylethyl)cyclohexyl]-2,4-difluoro-α-methyl-, Jun. 5, 2009, 1 page.

CAS Registry No. 1152826-22-6, Benzenemethanamine, 5-bromo-N-[4-(1,1-dimethylpropyl)cyclohexyl]-2-fluoro-, Jun. 7, 2009, 1 page.

CAS Registry No. 1154138-59-6, Benzenemethanamine, N-[4-(1,1-dimethylpropyl)cyclohexyl]-2,5-difluoro-, Jun. 9, 2009, 1 page.

CAS Registry No. 127456-43-3, Phenol, 2-[[[4-(1,1-dimethylethyl)cyclohexyl]amino]methyl]-4-(1,1-dimethylpropyl)-, trans-(9CI), Jun. 1, 1990, 1 page.

CAS Registry No. 127456-44-4, 1H-Inden-5-ol, 6-[[[4-(1,1-dimethylethyl)cyclohexyl]amino]methyl]-2,3-dihydro-, trans-(9CI), Jun. 1, 1990, 1 page.

CAS Registry No. 127456-45-5, Phenol, 4-(1,1-dimethylethyl)-2-[[[4-(1,1-dimethylethyl)cyclohexyl]amino]methyl]-, trans-(9CI), Jun. 1, 1990, 1 page.

CAS Registry No. 127456-46-6, Phenol, 4-(1,1-dimethylethyl)-2-[[[4-(1,1-dimethylethyl)cyclohexyl]amino]methyl]-6-methyl-, hydrochloride, trans-(9CI), Jun. 1, 1990, 1 page.

CAS Registry No. 127456-52-4, Phenol, 2-[[[4-(1,1-dimethylethyl)cyclohexyl]amino]methyl]-4-(1-methylethyl)-, cis-(9CI), Jun. 1, 1990, 1 page.

CAS Registry No. 127456-56-8, Phenol, 4-chloro-2-[[[4-(1,1-dimethylethyl)cyclohexyl]amino]methyl]-, trans-(9CI), Jun. 1, 1990, 1 page.

CAS Registry No. 127456-57-9, Phenol, 2-[[[4-(1,1-dimethylethyl)cyclohexyl]amino]methyl]-4-fluoro-, trans-(9CI), Jun. 1, 1990, 1 page.

CAS Registry No. 1308467-14-2, 1,2-Benzenediol, 3-[[[4-(1,1-dimethylpropyl)cyclohexyl]amino]methyl]-, Jun. 10, 2011, 1 page.

CAS Registry No. 1405571-87-0, Benzenemethanamine, 2-bromo-N-[4-(1,1-dimethylpropyl)cyclohexyl]-5-fluoro-, Nov. 23, 2012, 1 page.

CAS Registry No. 1406541-63-6, Phenol, 2-chloro-4-[[[4-(1,1-dimethylpropyl)cyclohexyl]amino]methyl]-, Nov. 25, 2012, 1 page.

CAS Registry No. 1411655-23-6, Benzenemethanamine, N-[4-(1,1-dimethylpropyl)cyclohexyl]-2,3-difluoro-, Dec. 5, 2012, 1 page.

CAS Registry No. 1456349-79-3, Benzenemethanamine, 2,3-dichloro-N-[4-(1,1-dimethylpropyl)cyclohexyl]-, Oct. 6, 2013, 1 page.

CAS Registry No. 1458497-71-6, Benzenemethanamine, 2,4-dichloro-N-[4-(1,1-dimethylethyl)cyclohexyl]-α-methyl-, Oct. 15, 2013, 1 page.

CAS Registry No. 1459328-13-2, Phenol, 2-bromo-4-[[[4-(1,1-dimethylpropyl)cyclohexyl]amino]methyl]-, Oct. 16, 2013, 1 page.

(56) References Cited

OTHER PUBLICATIONS

CAS Registry No. 1490220-45-5, Benzenemethanamine, 2-bromo-5-chloro-N-[4-(1,1-dimethylpropyl)cyclohexyl]-, Dec. 8, 2013, 1 page.
CAS Registry No. 1515984-46-9, Benzamide, N-(4-aminocyclohexyl)-3-chloro-N,5-dimethyl-, Jan. 10, 2014, 1 page.
CAS Registry No. 1542027-51-9, Phenol, 3-chloro-2-[[[4-(1,1-dimethylpropyl)cyclohexyl]amino]methyl]-, Feb. 11, 2014, 1 page.
CAS Registry No. 1624268-56-9, Benzamide, 4-[[[4-(1,1-dimethylethyl)cyclohexyl]amino]methyl]-N-methyl-, Sep. 22, 2014, 1 page.
CAS Registry No. 1712122-27-4, Benzenemethanamine, 5-chloro-N-[4-(1,1-dimethylpropyl)cyclohexyl]-2-fluoro-, May 25, 2015, 1 page.
CAS Registry No. 1772618-27-5, Phenol, 3-[[[4-(1,1-dimethylpropyl)cyclohexyl]amino]methyl]-5-fluoro-, Jun. 3, 2015, 1 page.
CAS Registry No. 1775706-37-0, Phenol, 2-chloro-6-[[[4-(1,1-dimethylpropyl)cyclohexyl]amino]methyl]-, Jun. 8, 2015, 1 page.
CAS Registry No. 1858436-76-6, Bicyclo[3.1.0]hexan-2-amine, N-[(3-chloro-5-methylphenyl)methyl]-, Feb. 3, 2016, 1 page.
CAS Registry No. 1931388-10-1, Benzenemethanamine, 2,5-dichloro-N-[4-(1,1-dimethylpropyl)cyclohexyl]-, Jun. 14, 2016, 1 page.
CAS Registry No. 1939264-55-7, Phenol, 4-[[[4-(1,1-dimethylpropyl)cyclohexyl]amino]methyl]-2-fluoro-, Jun. 26, 2016, 1 page.
CAS Registry No. 1939792-99-0, Benzenemethanamine, 5-bromo-2-chloro-N-[4-(1,1-dimethylpropyl)cyclohexyl]-, Jun. 27, 2016, 1 page.
CAS Registry No. 1962333-15-8, Benzenemethanamine, N-[4-(1,1-dimethylpropyl)cyclohexyl]-5-fluoro-2-methyl-, Jul. 29, 2016, 1 page.
CAS Registry No. 2032268-58-7, Cyclohexanecarboxylic acid, 4-[[(3-chloro-5-methylphenyl)methyl]amino]-, Nov. 15, 2016, 1 page.
CAS Registry No. 2199998-08-6, Cyclohexanecarboxylic acid, 2-[[(3-chloro-5-methylphenyl)methyl]amino]-1-methyl-, Mar. 27, 2018, 1 page.
CAS Registry No. 2202151-69-5, Cyclohexanecarboxylic acid, 3-[[(3-chloro-5-methylphenyl)methyl]amino]-, Mar. 30, 2018, 1 page.
CAS Registry No. 2322790-81-6, Benzenemethanamine, N-[4-(1,1-dimethylethyl)cyclohexyl]-3-(trifluoromethyl)-, Jun. 2, 2019, 1 page.
CAS Registry No. 2419600-39-6, Benzenemethanamine, 3-chloro-N-[4-(1,1-dimethylpropyl)cyclohexyl]-5-methyl-, Jun. 5, 2020, 1 page.
CAS Registry No. 415970-94-4, Benzenemethanamine, N-[4-(1,1-dimethylethyl)cyclohexyl]-3,5-dimethoxy-, May 15, 2002, 1 page.
CAS Registry No. 744981-83-7, Phenol, 2,6-dibromo-4-[[[4-(1,1-dimethylethyl)cyclohexyl]amino]methyl]-, Sep. 15, 2004, 1 page.
CAS Registry No. 793633-39-3, Phenol, 4-(1, 1-dimethylethyl)-2-[[[trans-4-(1,1-dimethylethyl)cyclohexyl]amino]methyl]-6-methyl-, Dec. 6, 2004, 1 page.
Cayman Chemical, "Safety Data Sheet", Caymanchem.com, Apr. 21, 2021, [online] available at: https://cdn.caymanchem.com/cdn/msds/33586m.pdf. 6 printed pages.
Chadeayne, Andrew R. et al., "The Crystal Structure of 4-AcO-DMT Fumarate." Psychedelic Science Review, Science Review Team, Mar. 25, 2019, 11 pages.
Chegaev, et al., "NO-donor melatonin derivatives: synthesis and in vitro pharmacological characterization", J Pineal Res. Apr. 2007; 42(4): 371-85.
Chen, et al., "Structure-activity relationships in a series of 5-[(2, 5-dihydroxybenzyl) amino] salicylate inhibitors of EGF-receptor-associated tyrosine kinase: importance of additional hydrophobic aromatic interactions", Journal of Medicinal Chemistry, Mar. 1994, pp. 845-859.
ClinicalTrials.gov, "Effects of Dimethyltryptamine in Healthy Subjects (DMT)", Apr. 20, 2020, 9 pages. Retrieved on Jun. 24, 2022 from https://clinicaltrials.gov/ct2/show/NCT04353024.
Cocchi et al., "Novel Psychoactive Phenethylamines: Impact on Genetic Material", International Journal of Molecular Sciences, 2020, 17 pages.
Corne. "A possible correlation between drug-induced hallucinations in man and a behavioural response in mice." Psychopharmacologia (Berl.), 1967; 11: 65-78.
Cozzi, Nicholas V. et al., "Synthesis and characterization of high-purity N,N-dimethyltryptamine hemifumarate for human clinical trials." Drug Test Anal. Oct. 2020; 12(10): 1483-1493. doi: 10.1002/dta.2889. Epub Jul. 14, 2020.
Dakic et al., "Short term changes in the proteome of human cerebral organoids induced by 5-MeO-DMT", Scientific Reports, 2017, 13 pages.
Dalgleish, T., et al., "Transdiagnostic Approaches to Mental Health Problems: Current Status and Future Directions." Journal of Consulting and Clinical Psychology, 2020, vol. 88, No. 3, 179-195.
Database Registry [Online] Chemical Abstract Service, Columbus, Ohio, US; retrieved from STN Database accession No. 2107153-36-4, Aug. 2, 2017 (Aug. 2, 2017), 3 pages.
Davis et al., "5-methoxy-N, N-dimethyltryptamine (5-MeO-DMT) used in a naturalistic group setting is associated with unintended improvements in depression and anxiety", The American Journal of Drug and Alcohol Abuse, 2019, 10 pages.
Davis, et al., "The epidemiology of 5-methoxy-N, N-dimethyltryptamine (5-MeO-DMT) use: Benefits, consequences, patterns of use, subjective effects, and reasons for consumption", J Psychopharmacol, Jul. 2018; 32(7): 779-792. Epub Apr. 30, 2018.
De Barros et al., "Synthesis of 25X-BOMes and 25X-NBOHs (X = H, I, Br) for pharmacological studies and as reference standards for forensic purposes," Tetrahedron Letters, Mar. 2021, 4 pages.
Declaration of Majed Fawaz under 37 C.F.R. § 1.130, in U.S. Appl. No. 17/824,861, dated Jun. 2024, 2 pages.
Dimoitou, "Nasal spray" #3 Posted: Jun. 27, 2014 6:58:57 pm DMT-Nexus, Jun. 27, 2014, https://forum.dmt-nexus.me/threads/nasal-spray.343226/. 5 pages.
Dunlap et al., "Identification of psychoplastogenic N, N-dimethylaminoisotryptamine (isoDMT) analogues through structure-activity relationship studies", J. Med. Chem. 2020, pp. 1142-1155.
Dunlap, Lee, E. et al., "Reaction of N,N-Dimethyltryptamine with Dichloromethane Under Common Experimental Conditions." ACS Omega, 2018, 3, 4968-4973.
Durham, "Regulation of calcitonin gene-related peptide secretion by a serotonergic antimigraine drug", The Journal of Neuroscience, May 1, 1999, pp. 3423-3429.
European Patent Office, Extended Search Report, EP Application Serial No. 21800237.6, Apr. 15, 2024. 8 pages.
Extended European Search Report for EP Application No. 22812068.9, dated Mar. 28, 2025, 13 pages.
Extended European Search Report for European Application No. 22796577.9 mailed Mar. 10, 2025, 10 pages.
Falkenberg et al., "The crystal and molecular structure of (N,N)-dimethyltryptamine." Acta Crystallogr., Sect B28, 3075-3083, Mar. 9, 1972, 9 pages.
Gaujac et al. "Determination of N,N-dimethyltryptamine in beverages consumed in religious practices by headspace solid-phase microextraction followed by gas chromatography ion trap mass spectrometry," Talanta. Mar. 15, 2013: 106:394-8. doi: 10.1016/j.talanta.2013.01.017. Epub Feb. 1, 2013.
Gaujac et al., "Investigations into the polymorphic properties of N, N-dimethyltryptamine by X-ray diffraction and differential scanning calorimetry," Microchemical Journal 110, Mar. 2, 2013, 12 pages.
Glatfelter G, et al., "Synthesis, Structural Characterization, and Pharmacological Activity of Novel Quaternary Salts of 4-Substituted Tryptamines", ACS Omega, Jul. 2022, vol. 7(28), pp. 24888-24894.
Glennon et al., "Influence of amine substituents on 5-HT2A versus 5-HT2C binding of phenylalkyl-and indolylalkylamines", Journal of Medicinal Chemistry, 1994, pp. 1929-1935.
Glennon et al., "Synthesis and evaluation of a novel series of N,N-dimethylisotryptamines", J Med Chem. Jan. 1984; 27(1): 41-5.
Glennon, R. A., et al., "Hallucinogens as discriminative stimuli: A comparison of 4-OMe and 5-OMe DMT with their methylthio

(56) References Cited

OTHER PUBLICATIONS counterparts", Life Science, Pergamon Press, Oxford, GB, vol. 30, No. 5, Feb. 1, 1982 (Feb. 2, 1982), pp. 465-467.
Gonzalez-Maeso et al., "Hallucinogens Recruit Specific Cortical 5-HT2A Receptor-Mediated Signaling Pathways to Affect Behavior," Neuron, Feb. 2007, 53, 439-452.
Gribble, "Recent developments in indole ring synthesis-methodology and applications", Journal of the Chemical Society, Perkin Transactions, 2000, pp. 1045-1075.
Griffiths et al., "Psilocybin produces substantial and sustained decreases in depression and anxiety in patients with life-threatening cancer: a randomized double-blind trial", Journal of Psychopharmacology (2016); 30: 1181-1197. doi: 10.1177/0269881116675513.
Grundke et al., "Photochemical α-Aminonitrile Synthesis Using Zn-Phthalocyanines as Near-Infrared Photocatalysts", J Org Chem. May 6, 2022; 87(9): 5630-5642, with supporting info. Epub Apr. 14, 2022. 60 pages.
Gurevich and Gurevich, "GPCR Signaling Regulation: The Role of GRKs and Arrestins", Front Pharmacol. Feb. 19, 2019: 10: 125. eCollection 2019, 11 pages.
Halberstadt, A. L., "Recent Advances in the Neuropsychopharmacology of Serotonergic Hallucinogens", Behav Brain Res. Jan. 15, 2015: 277: 99-120. doi: 10.1016/j.bbr.2014.07.016. Epub Jul. 15, 2014. Author manuscript; available in PMC Jan. 15, 2016. 60 pages.
Halberstadt et al., "Differential contributions of serotonin receptors to the behavioral effects of indoleamine hallucinogens in mice", J Psychopharmacol. Nov. 2011; 25(11): 1548-61. Epub Dec. 8, 2010. Author manuscript; available in PMC Dec. 27, 2012. 25 pages.
Hamada et al., "Water-soluble prodrugs of dipeptide HIV protease inhibitors based on O→N intramolecular acyl migration: Design, synthesis and kinetic study", Bioorg Med Chem., Jan. 2004, pp. 159-170.
Hansen et al., "Synthesis and pharmacological evaluation of N-benzyl substituted 4-bromo-2,5-dimethoxyphenethylamines as 5-HT2A/2C partial agonists", Bioorganic & Medicinal Chemistry, 2015, pp. 3933-3937.
Hansen et al., "Synthesis and Structure-Activity Relationships of N-Benzyl Phenethylamines as 5-HT2A/2C Agonists", ACS Chemical Neuroscience, 2014, pp. 243-249.
Harriott et al., "Animal models of migraine and experimental techniques used to examine trigeminal sensory processing", J Headache Pain. Aug. 29, 2019; 20(1): 91. 15 pages.
Hart et al., "Melting Point Determination, Melting Range", Adapted from Organic Chemistry: A Short course, 13th ed. Houghton-Mifflin, Boston, 2012, available at: https://chemistry.sites.clemson.edu/organic/Labs/2270Docs/MeltingPoint.pdf, 4 pages.
Huang et al., "Nose-to-brain delivery of drug nanocrystals by using Ca2+ responsive deacetylated gellan gum based in situ-nanogel." International Journal of Pharmaceuticals. 2020; S0378-5173(20)31167-4. 41 pages.
Humphrey et al., "Practical methodologies for the synthesis of indoles", Chem Rev. Jul. 2006; 106(7): 2875-911, 37 pages.
Huttunen, et al., "Prodrugs—from Serendipity to Rational Design", Pharmacological Reviews, vol. 63, No. 3, Sep. 2011, pp. 750-771.
International Preliminary Report on Patentability for International Application No. PCT/US2022/026396 dated Nov. 9, 2023, 8 pages.
International Preliminary Report on Patentability for International Application No. PCT/US2022/030912 dated Dec. 7, 2023, 10 pages.
International Preliminary Report on Patentability for International Application No. PCT/US2022/032918 dated Dec. 21, 2023, 7 pages.
International Preliminary Report on Patentability for International Application No. PCT/US2022/045336, mailed Apr. 11, 2024, 7 pages.
International Preliminary Report on Patentability for International Application No. PCT/US2022/047520 mailed May 10, 2024, 8 pages.
International Preliminary Report on Patentability for International Application No. PCT/US2023/073574 mailed Mar. 20, 2025, 9 pages.
International Search Report and Written Opinion for International Application No. PCT/US2022/026396, mailed Jul. 28, 2022, 10 pages.
International Search Report and Written Opinion for International Application No. PCT/US2022/030912, mailed Oct. 5, 2022, 20 pages.
International Search Report and Written Opinion for International Application No. PCT/US2022/032715 mailed Nov. 17, 2022, 18 pages.
International Search Report and Written Opinion for International Application No. PCT/US2022/032918, mailed Oct. 12, 2022, 10 pages.
International Search Report and Written Opinion for International Application No. PCT/US2022/045336 dated Jan. 13, 2023, 14 pages.
International Search Report and Written Opinion for International Application No. PCT/US2022/082465 dated Jun. 6, 2023, 11 pages.
International Search Report and Written Opinion for International Application No. PCT/US2023/073574 dated Feb. 16, 2024, 13 pages.
International Search Report and Written Opinion for International Application No. PCT/US2023/077879, mailed Apr. 4, 2024, 11 pages.
International Search Report and Written Opinion for International Application No. PCT/US2023/082080, mailed Apr. 4, 2024, 8 pages.
International Search Report and Written Opinion for International Application No. PCT/US2024/026797 mailed Sep. 6, 2024, 10 pages.
International Search Report and Written Opinion for International Application No. PCT/US2024/049678, mailed Jan. 21, 2025, 9 pages.
International Search Report and Written Opinion for International Application No. PCT/US2025/014571 mailed Mar. 21, 2025, 15 pages.
International Search Report and Written Opinion for PCT Application No. PCT/US2021/031215 mailed Oct. 1, 2021, 10 pages.
International Search Report and Written Opinion for PCT Application No. PCT/US2022/047520 mailed Mar. 1, 2023, 11 pages.
International Search Report and Written Opinion for PCT Application No. PCT/US2023/084319 mailed May 20, 2024, 13 pages.
International Search Report and Written Opinion for PCT Application No. PCT/US2024/036639 mailed Sep. 23, 2024, 11 pages.
International Search Report and Written Opinion for PCT Application No. PCT/US2024/038804 mailed Dec. 17, 2024, 14 pages.
International Search Report and Written Opinion for PCT Application No. PCT/US2024/039503 mailed Nov. 5, 2024, 17 pages.
International Search Report and Written Opinion for PCT Application No. PCT/US2024/045494 mailed Nov. 15, 2024, 11 pages.
Invitation to Pay Additional Fees for International Application No. PCT/US2022/030912, mailed Jul. 28, 2022, 8 pages.
Invitation to Pay Additional Fees for International Application No. PCT/US2022/032918, mailed Aug. 12, 2022, 2 pages.
Invitation to pay additional fees for International Application No. PCT/US2023/073574, dated Nov. 6, 2023, 2 pages.
Invitation to Pay Additional Fees for International Application No. PCT/US2024/026797 mailed Jun. 25, 2024, 2 pages.
Invitation to Pay Additional fees for International Application No. PCT/US2024/038804, mailed Sep. 23, 2024, 3 pages.
Invitation to pay additional fees for International Application No. PCT/US2024/039503, dated Sep. 10, 2024, 2 pages.
Invitation to Pay Additional Pay Fees for International Application No. PCT/US2024/061478 mailed Feb. 25, 2025, 2 pages.
Invitation to Pay Additional Pay Fees for International Application No. PCT/US22/47520, mailed Jan. 3, 2023, 2 pages.
Invitation to Pay Fee for International Application No. PCT/US2022/082465 dated Mar. 16, 2023, 3 pages.
Kaminska et al., "25C-NBOMe short characterization", Forensic Toxicology, 2020, pp. 490-495.

(56) References Cited

OTHER PUBLICATIONS

Klein et al., "Toward selective drug development for the human 5-hydroxytryptamine 1E receptor: a comparison of 5-hydroxytryptamine 1E and 1F receptor structure-affinity relationships", J Pharmacol Exp Ther. Jun. 2011; 337(3): 860-7. Epub Mar. 21, 2011.
Klein, et al, "Structure-activity relationships in potentially hallucinogenic N, N-dialkyltryptamines substituted in the benzene moiety", J. Med. Chen, Aug. 1982, pp. 908-913.
Kraehenmann. "Dreamlike effects of LSD on waking imagery in humans depend on serotonin 2A receptor activation." Psychopharmacol (Berl), 2017; 234: 2031-2046.
Kraehenmann. "LSD Increases Primary Process Thinking via Serotonin 2A Receptor Activation." Front Pharmacol 2017; 8: 814; 9 pages.
Krise, J. P., et al., "Novel prodrug approach for tertiary amines: synthesis and preliminary evaluation of N-phosphonooxymethyl prodrugs", J Med Chem. Aug. 12, 1999; 42(16): 3094-100.
Kucklander, et al., "Darstellung und Oxidation von 2-(2, 5-Dihydroxy-phenyl)-ethylamin-Derivaten, II/Synthesis and Oxidation of 2-(2, 5-Dihydroxyphenyl)-ethylamine Derivatives, II", Zeitschrift für Naturforschung B, 1987, pp. 1567-1577 (with English abstract). 12 pages.
Li et al., "Treatment of breast and lung cancer cells with a N-7 benzyl guanosine monophosphate tryptamine phosphoramidate pronucleotide (4Ei-1) results in chemosensitization to gemcitabine and induced elF4E proteasomal degradation", Mol Pharm., Feb. 2013, pp. 523-531.
Lima da Cruz et al., "Corrigendum: A Single Dose of 5-MeO-DMT Stimulates Cell Proliferation, Neuronal Survivability, Morphological and Functional Changes in Adult Mice Ventral Dentate Gyrus", Front. Mol. Neurosci., 2018, 11 pages.
Lyon et al., "Indolealkylamine analogs share 5-HT2 binding characteristics with phenylalkylamine hallucinogens", European Journal of Pharmacology, 1988, pp. 291-297.
Madsen et al., "Psilocybin-induced reduction in chronic cluster headache attack frequency correlates with changes in hypothalamic functional connectivity", medRxiv. Jul. 10, 2022: Jul. 2022.
Madsen et al., "Psychedelic effects of psilocybin correlate with serotonin 2A receptor occupancy and plasma psilocin levels," Neuropsychopharmacology (2019) 44: 1328-1334.
Mahalingam, "Semisolid Dosages: Ointments, Creams, and Gels." in Pharmaceutical Manufacturing Handbook: Production and Processes. (Chapter 9, 267-312), Shayne C. Gad ed., John Wiley & Sons, Inc. 2008.
Malaca S et al., "Toxicology and Analysis of Psychoactive Tryptamines", International Journal of Molecular Science, Dec. 2020, vol. 21(23), pp. 1-30.
McBride, "Bufotenine: Toward an Understanding of Possible Psychoactive Mechanisms", Journal of Psychoactive Drugs, Jul.-Sep. 2000, pp. 321-331.
Mcclure-Begley and Roth, "The promises and perils of psychedelic pharmacology for psychiatry", Nat Rev Drug Discov. Jun. 2022; 21(6): 463-473. Epub Mar. 17, 2022.
Mertens and Preller, "Classical Psychedelics as Therapeutics in Psychiatry—Current Clinical Evidence and Potential Therapeutic Mechanisms in Substance Use and Mood Disorders", Pharmacopsychiatry. Jul. 2021; 54(4): 176-190. Epub Jan. 20, 2021.
Milne et al., "Metabolic engineering of *Saccharomyces cerevisiae* for the de novo production of psilocybin and related tryptamine derivatives", Metabolic Engineering, Jul. 2020, pp. 25-36.
Mithoefer et al., "The safety and efficacy of {+/−}3,4-methylenedioxymethamphetamine-assisted psychotherapy in subjects with chronic, treatment-resistant posttraumatic stress disorder: the first randomized controlled pilot study." J Psychopharmacol. Apr. 2011; 25(4): 439-52. doi: 10.1177/0269881110378371. Epub Jul. 19, 2010.
Mokler D J et al: "The 5HT"2 antagonist pirenperone reverses disruption of FR-40 by hallucinogenic drugs." Pharmacology Biochemistry and Behavior, Elsevier, US, vol. 22, No. 5, May 1, 1985 (May 1, 1985), pp. 677-682.
National Center for Biotechnology Information, "1-[3-[2-(dimethylamino) ethyl]-1H-indol-4-yl]-N-methylmethanesulfonamide: Pubchem CID 149771082" Pubchem entry (online), pp. 1-8, Aug. 12, 2020; from the Internet: [URL: https://pubchem.ncbi.nim.nih.gov/compound/149771082).
National Center for Biotechnology Information (2023). PubChem Substance Record for SID 309311543, SID 309311543, Source: Aurora Fine Chemicals LLC. Modified Jan. 30, 2016, retrieved from https://pubchem.ncbi.nlm.nih.gov/substance/309311543, 5 pages.
National Center for Biotechnology Information "[2-bromo-3-[2-(dimethylamino) ethyl]-1H-indol-4-yl] acetate: Pubchem CID 157042555" Pubchem entry (online), Nov. 30, 2021, 9 pages.
National Center for Biotechnology Information, "3-[2-(dimethylamino) ethyl)-2-fluoro-1H-indol-4-ol: Pubchem CID 162478135" Pubchem entry (online), Feb. 6, 2022; Retrieved from the Internet: [URL: https://pubchem.ncbi.nlm.nih.gov/compound/162478135). 9 pages.
National Center for Biotechnology Information, "[3-[2-(dimethylamino) ethyl]-2-fluoro-1H-indol-4-yl]acetate: Pubchem CID 162478146" Pubchem entry (online), pp. 1-8, Feb. 6, 2022.
National Center for Biotechnology Information, "[3[2-[di(propan-2-yl)amino] ethyl)-1H-indol-4-yl) dihydrogen phosphate: Pubchem CID 166138444" Pubchem entry (online), pp. 1-7. Dec. 20, 2022. [URL: https://pubchem.ncbi.nlm.nih.gov/compound/166138444].
National Center for Biotechnology Information, "4-Acetoxy-N,N-diisopropyltryptamine: Pubchem CID 24801868" Pubchem entry Jun. 6, 2008; retrieved from the Internet: [URL: https://pubchem.ncbi.nlm.nih.gov/compound/24801868), 21 pages.
National Center for Biotechnology Information. PubChem Compound Summary for CID 24802108, N-Isopropyl-N-(2-(4-methoxy-1H-indol-3-yl)ethyl)propan-2-amine. https://pubchem.ncbi.nlm.nih.gov/compound/24802108. Create: Jun. 6, 2008, Modify: Mar. 29, 2025, Accessed Apr. 5, 2025. 13 pages.
Nichols, "Hallucinogens", Pharmacol. Ther., 2004, pp. 131-181.
Nichols, "Structure-Activity Relationships of Phenethylamine Hallucinogens", J. Pharm. Sciences, 1981, pp. 839-849.
Olson, David E., "The Subjective Effects of Psychedelics May Not Be Necessary for Their Enduring Therapeutic Effects", ACS Pharmacol Transl Sci. Apr. 9, 2021; 4(2): 563-567. Published online Dec. 10, 2020.
Ott, J., "Pharmepena-psychonautics: human intranasal, sublingual and oral pharmacology of 5-methoxy-N, N-dimethyl-tryptamine." Journal of Psychoactive Drugs, Dec. 2001, pp. 403-407.
Ott, J., "Pharmañopo—Psychonautics: Human intranasal, sublingual, intrarectal, pulmonary and oral pharmacology of bufotenine." Journal of Psychoactive Drugs, Sep. 2001, pp. 273-281.
Pandy-Szekeres et al., "GPCRdb in 2023: state-specific structure models using AlphaFold2 and new ligand resources", Nucleic Acids Res. Jan. 6, 2023; 51(D1): D395-D402. 8 pages.
Perez Custodio et al., "25B-NBOMe, a novel N-2-methoxybenzyl-phenethylamine (NBOMe) derivative, may induce rewarding and reinforcing effects via a dopaminergic mechanism: evidence of abuse potential", Addiction Biology, Nov. 2019, 12 pages.
Pokorny et al., "Modulatory effect of the 5-HT1A agonist buspirone and the mixed non-hallucinogenic 5-HT1A/2A agonist ergotamine on psilocybin-induced psychedelic experience." Eur. Neuropsychopharmacol., Apr. 2016, pp. 756-766.
Pottie et al., "Identification of psychedelic new psychoactive substances (NPS) showing biased agonism at the 5-HT2AR through simultaneous use of β-arrestin 2 and miniGαq bioassays", Biochem Pharmacol. Dec. 2020: 182: 114251. Epub Sep. 28, 2020. 37 pages.
Preller et al., "Effects of serotonin 2A/1A receptor stimulation on social exclusion processing," PNAS, May 3, 2016, vol. 113, No. 18, 5119-5124.
Preller et al., "Role of the 5-HT2A Receptor in Self- and Other-Initiated Social Interaction in Lysergic Acid Diethylamide-Induced States: A Pharmacological fMRI Study", Journal of Neuroscience (Apr. 2018); 38(14): 3603-3611. doi: 10.1523/JNEUROSCI.1939-17.2018. Epub Mar. 19, 2018.
Preller. "The fabric of meaning and subjective effects in LSD-induced states depend on serotonin 2A receptor activation", Current Biology (2017); 27(3): 451-457. doi: 10.1016/j.cub.2016.12.030. Epub Jan. 26, 2017.

(56) References Cited

OTHER PUBLICATIONS

Prescribing information for Brevibloc (Esmolol Hydrochloride): www.baxterpi.com/pi-pdf/Brevibloc_PI.pdf), Initial U.S. approval: 1986, revised Apr. 2018, 19 pages.
Pubchem CID 15274381, Created Date—Feb. 9, 2007, Modified Date—Jan. 25, 2025, 14 pages.
Pubchem CID 156821129, created Nov. 20, 2021, Modify date Aug. 23, 2024, available at: https://pubchem.ncbi.nlm.nih.gov/compound/156821129, 10 pages.
Pubchem CID 6089, Dimethyltryptamine, Create date: Mar. 26, 2005 (Mar. 26, 2005), 6 pages.
Pubchem CID 88309097, Created date Feb. 12, 2015, Modified date Nov. 9, 2024, available at: https://pubchem.ncbi.nlm.nih.gov/compound/88309097, 8 pages.
Pubchem, SID 310331158, Modify Date: Feb. 15, 2015, 4 pages.
Pubchem, SID 369863280, Modify Date: May 25, 2018, 5 pages.
Pubchem, SID 385740476, 2-(2,5-dimethoxy-4-(propan-2-yt)phenyl)-N-(2methoxybenzyl)ethanamine, Sep. 23, 2019, 6 pages, retrieved from https://pubchem.ncbi.nlm.nih.gov/substance/385740476.
Pubchem, SID 433987242, Available Date: Sep. 28, 2020. Retrieved from the Internet: URL:https://pubchem.ncbi.nlm.nih.gov/substance/433987242, 7 pages.
Pubchem, SID 627609, Modify Date: Jan. 21, 2015. Retrieved from the Internet: https://pubchem.ncbi.nlm.nih.gov/substance/627609. 8 pages.
Pubchem, Substance Record for SID 313512691, Available Date Jun. 11, 2016. Retrieved from the Internet URL:https://pubchem.ncbi.nlm.nih.gov/sustance/313512691. 5 pages.
Pubchem, Substance Record for SID 471368824 Available Date Sep. 27, 2002. Retrieved from the Internet URL:https://pubchem.ncbi.nlm.nih.gov/sustance/471368824. 5 pages.
Pubchem, Substance Record for SID 474211406 Available Date Dec. 15, 2002. Retrieved from the Internet URL:https://pubchem.ncbi.nlm.nih.gov/sustance/474211406. 5 pages.
Pubmed Compound Record for CID 123606, Almotriptan, U.S. National Library of Medicine, Aug. 8, 2005, (https://pubchem.ncbi.nlm.nih.gov/compound/123606). 53 pages.
Pubmed Compound Record for CID 84056101, 2-(2-Chloro-4-methoxy-1H-indol-3-yl)ethyanamine, U.S. National Library of Medicine, Oct. 20, 2014, pp. 1-7, (https://pubchem.ncbi.nlm.nih.gov/compound/84056101).
Pubmed Compound Record for CID 84058691, 1-(2-Chloro-4-methoxy-1H-indol-3-yl)propan-2-amine, U.S. National Library of Medicine, Oct. 20, 2014, pp. 1-7, (https://pubchem.ncbi.nlm.nih.gov/compound/84058691).
Puledda et al., "An update on migraine: current understanding and future directions," J Neurol (2017) 264:2031-2039.
Puri et al., "Thiolation of Biopolymers for Developing Drug Delivery Systems with Enhanced Mechanical and Mucoadhesive Properties: A Review." Polymers (Basel). Aug. 11, 2020;12(8): 1803. doi: 10.3390/polym12081803. 27 pages.
Ray, T., "Psychedelics and the Human Receptorome," PLoS One (2010) 5(2): e9019, 17 pages.
Riba, et al., "Metabolism and urinary disposition of N,N-dimethyltryptamine after oral and smoked administration: a comparative study", Drug Test Anal. May 2015;7(5): 401-6. Epub Jul. 28, 2014.
Roth et al., "High-affinity Agonist Binding Is Not Sufficient for Agonist Efficacy at 5-Hydroxytryptamine2A Receptors: Evidence in Favor of a Modified Ternary Complex Model", The Journal of Pharmacology and Experimental Therapeautics, 1997, vol. 280, No. 2, pp. 576-583.
Ruiz et al., "Routes of Drug Administration: Dosage, Design, and Pharmacotherapy Success", In book: ADME Processes in Pharmaceutical Sciences, Chapter 6, Jan. 2018, DOI:10.1007/978-3-319-99593-9_6, 44 pages.
Santos-Longhurst, A, "How Long Does DMT Last?" Healthline.com, Nov. 24, 2019, [online] retrieved on Jun. 24, 2022, from https://www.healthline.com/health/how-long-does-dmt-last, 12 pages.
Sargent et al., "Radiohalogen-Labeled Imaging Agents. 3. Compounds for Measurement of Brain Blood Flow by Emission Tomography," Journal of Medicinal Chemistry (1984), 27(8), 1071-1077.
Schifano et al., "New psychoactive substances (NPS) and serotonin syndrome onset: A systematic review", Exp Neurol. May 2021: 339: 113638. Epub Feb. 8, 2021. 29 pages.
Schindler et al., "Exploratory Controlled Study of the Migraine-Suppressing Effects of Psilocybin", Neurotherapeutics, Jan. 2021; 18(1): 534-543. Epub Nov. 12, 2020. 10 pages.
Shen et al., "Psychedelic 5-Methoxy-N,N-dimethyltryptamine: Metabolism, Pharmacokinetics, Drug Interactions, and Pharmacological Actions", Curr Drug Metab., Oct. 2010 ; 11(8): 659-666.
Shen L, et al., "Bufotenines-loaded liposome exerts anti-inflammatory, analgesic effects and reduce gastrointestinal toxicity through altering lipid and bufotenines metabolism", Biomed Pharmacother, Sep. 2022, vol. 153, pp. 1-12.
Sherwood. "Synthesis and characterization of 5-MeO-DMT succinate for clinical use", ACS Omega (2020); 5(49): 32067-32075. doi: 10.1021/acsomega.0c05099.
Sigma, Succinic acid—Butanedioic acid, CAS No. 110-15-6, Merck KGaA, 2023, 4 pages.
Sizemore, T.R, and Dacks, A.M., "Circadian Clocks: Mosquitoes Master the Dark Side of the Room", Curr Biol. Aug. 17, 2020; 30(16): R932-R934. 3 pages.
Strassman, "Dose-response study of N,N-dimethyltryptamine in humans. I. Neuroendocrine, autonomic, and cardiovascular effects", Arch Gen Psychiatry. Feb. 1994; 51(2): 85-97.
Strassman, "N-dimethyltryptamine in humans: II. Subjective effects and preliminary results of a new rating scale", Arch Gen Psychiatry. Feb. 1994; 51(2): 98-108.
Terry, Alvin V., "Drugs that target serotonergic receptors", Cognitive Enhancing Drugs, Introduction, pp. 79-80, 2004, 2 pages.
The product Item No. 33586 of Cayman Chemical, Apr. 2021, 1 page.
Thoai, et al., "Design and Synthesis of Sustain-Acting Melatonin Prodrugs", Sep. 12, 2013 (Sep. 12, 2013), Journal of Chemistry, vol. 2013, Issue 1, pp. 1-6.
Tirapegui et al., "Synthesis of N-(halogenated) benzyl analogs of superpotent serotonin ligands," J. Chil. Chem. Soc., (2014) 59, No. 3, pp. 2625-2627.
Titeler. "Radioligand binding evidence implicates the brain 5 HT2 receptor as a site of action for LSD and phenylisopropylamine hallucinogens." Psychopharmacol, 1988; 94: 213-216.
Tomaszewski et al., "Benzofuran Bioisosteres of Hallucinogenic Tryptamines," J. Med. Chem., 1992, 35, pp. 2061-2064.
United States Patent and Trademark Office, International Search Report and Written Opinion for PCT/US2022/45336, Jan. 13, 2023, 14 pages.
Uthaug et al., "A single inhalation of vapor from dried toad secretion containing 5-methoxy-N,N-dimethyltryptamine (5-MeO-DMT) in a naturalistic setting is related to sustained enhancement of satisfaction with life, mindfulness-related capacities, and a decrement of psychopathological symptoms," Psychopharmacology (2019) 236:2653-2666.
Uthaug et al., "Prospective examination of synthetic 5-methoxy-N,N-dimethyltryptamine inhalation: effects on salivary IL-6, cortisol levels, affect, and non-judgment," Psychopharmacology (2020) 237:773-785.
Valle et al., "Inhibition of alpha oscillations through serotonin-2A receptor activation underlies the visual effects of ayahuasca in humans", European Neuropsychopharmacology (2016); 26(7): 1161-1175. doi: 10.1016/j.euroneuro.2016.03.012. Epub Mar. 25, 2016.
Viracocha, "The DMT Handbook." Dec. 2008, URL:https://catbull.com/alamut/Bibliothek/DMT_Handbook.pdf. 31 pages.
Vollenweider et al., "Psilocybin induces schizophrenia-like psychosis in humans via a serotonin-2 agonist action", Neuroreport (1998); 9(17): 3897-3902. doi: 10.1097/00001756-199812010-00024.
Vollenweider et al., "Psychedelic drugs: neurobiology and potential for treatment of psychiatric disorders", Nature Reviews Neuroscience (2020); 21(11): 611-624. doi: 10.1038/s41583-020-0367-2. Epub Sep. 14, 2020.

(56) References Cited

OTHER PUBLICATIONS

Wang et al., "Anti-inflammatory and analgesic actions of bufotenine through inhibiting lipid metabolism pathway," Biomedicine & Pharmacotherapy (2021) 140: 111749, 11 pages.
Wey et al., "Structure-based design, synthesis, and biological evaluation of indomethacin derivatives as cyclooxygenase-2 inhibiting nitric oxide donors", Journal of medicinal chemistry, Dec. 2007, pp. 6367-6382.
Wikipedia, "Perfusion", Dec. 29, 2020 (Dec. 29, 2020), retrieved on Jun. 24, 2022 from https://en.wikipedia.org/w/index.php?title=Perfusion&oldid=996968059; 5 pages.
Winter et al., "Psilocybin-induced stimulus control in the rat", Pharmacology Biochemistry and Behavior (2007); 87(4): 472-480. doi: 10.1016/j.pbb.2007.06.003. Epub Jun. 22, 2007.
Winter et al., "The Paradox of 5-Methoxy-N, N-Dimethyltryptamine: An Indoleamine Hallucinogen That Induces Stimulus Control Via 5-HT1A Receptors," Pharmacology Biochemistry and Behavior, 2000, vol. 65, No. 1, pp. 75-82.
Wolff, M., "Burger's Medicinal Chemistry And Drug Discovery", Fifth Edition, John Wiley & Sons (1995); 1: 975-977.
Wood et al., "Prevalence of use and acute toxicity associated with the use of NBOMe drugs", Clin Toxicol (Phila). Feb. 2015; 53(2): 85-92. doi:10.3109/15563650.2015.1004179.
Yu, A.M., "Indolealkylamines: Biotransformations and Potential Drug-Drug Interactions," The AAPS Journal, Jun. 2008, vol. 10, No. 2, pp. 242-253.
Zamberlan et al., "The Varieties of the Psychedelic Experience: A Preliminary Study of the Association Between the Reported Subjective Effects and the Binding Affinity Profiles of Substituted Phenethylamines and Tryptamines", Front Integr Neurosci. Nov. 8, 2018: 12: 54. eCollection 2018. 22 pages.
Baker et al., "Neuropharmacological and Neurochemical Properties of N-(2-Cyanoethyl)-2-Phenylethylamine, A Prodrug of 2-Phenylethylamine." Br J Pharmacol. Oct. 1987; 92(2): 243-55.
Cayman Chemical "Safety Data Sheet Acc. to OSHA HCS", N,N-DMT (Succinate), CAS No. 2853570-32-6, Cayman Chemical: pp. 1-7, Revised Feb. 15, 2024.
Daiber et al., "Organic Nitrate Therapy, Nitrate Tolerance, and Nitrate-Induced Endothelial Dysfunction: Emphasis on Redox Biology and Oxidative Stress." Antioxid Redox Signal. Oct. 10, 2015;23(11):899-942.
Du, M., "An Overview on Transmucosal Permeability and Formulation." J Develop Drugs. 13:227, (2024), 2 pages.
Extended European Search Report for European Application No. 22821070.4 mailed May 26, 2025, 11 pages.
Extended European Search Report for European Application No. 22877368.5 mailed Jun. 16, 2025, 9 pages.
Graeff F.G., et al., "Role of 5-HT in stress, anxiety and depression", Pharmacology Biochemistry and Behavior, Elsevier, US, vol. 54, No. 1, Jan. 1, 1996 (Jan. 1, 1996), pp. 129-141.
Gyermek L., "A New Class of 5-Hydroxytryptamine Antagonists", Journal of Medicinal Chemistry, vol. 7, Jan. 1, 1964 (Jan. 1, 1964), pp. 280-282.
Hasegawa et al., "A Novel Methodology for Preparing 5-chloro-and 5-bromo-tryptamines and tryptophans, and its Application to the Synthesis of (+/−)-bromochelonin BI." (1999), Heterocycles, vol. 51, No. 12, pp. 2815-2821.
Holze et al. "Distinct acute effects of LSD, MDMA, and Damphetamine in healthy subjects." Neuropsychopharmacology. Feb. 2020;45(3):462-471.
International Preliminary Report on Patentability for International Application No. PCT/US2023/084319 mailed Jun. 26, 2025, 9 pages.
International Preliminary Report on Patentability for PCT Application No. PCT/US2023/077879 mailed May 8, 2025, 9 pages.
International Preliminary Report on Patentability for PCT Application No. PCT/US2023/082080 mailed Jun. 12, 2025, 7 pages.
International Search Report and Written Opinion for PCT Application No. PCT/US2024/061478 mailed Apr. 23, 2025, 10 pages.
Invitation to Pay Additional fees for PCT Application No. PCT/US2025/026640, mailed Jun. 24, 2025, 2 pages.
Lambert, Geoffrey, A., "Looking in the wrong place? The search for an ideal migraine preventative", Drug Development Research, New York, NY, US, vol. 68, No. 6, Dec. 18, 2007 (Dec. 18, 2007), pp. 376-388, DOI: 10.1002/DDR.20204.
Lyon et al., "3, 4-Methylenedioxymethamphetamine (MDMA): stereoselective interactions at brain 5-$HT_1$ and 5-$HT_2$ receptors." Psychopharmacology (1986); 88: 525-526. doi: 10.1007/BF00178519.
Madhav, et al., "Orotransmucosal drug delivery systems: A review", Journal of Controlled Release (Nov. 16, 2009); 140(1): 2-11. doi:10.1016/j.jconrel.2009.07.016. Epub Aug. 6, 2009.
National Center for Biotechnology Information. PubChem Compound Summary for CID 10624, Psilocybin. https://pubchem.ncbi.nlm.nih.gov/compound/Psilocybin. Create date Mar. 3, 2005, Accessed May 5, 2025. 62 pages.
Nichols, D. E., "Psychedelics." Pharmacol Rev. Apr. 2016;68(2):264-355.
Oliver et al., "Beta-blockers: Historical Perspective and Mechanisms of Action." Rev Esp Cardiol (Engl Ed). Oct. 2019; 72(10): 853-862).
Pandy-Szekeres et al., "The G Protein Database, GproteinDb." Nucleic Acids Res. Jan. 7, 2022; 50(D1): D518-D525.
Schlag et al., "Adverse effects of psychedelics: From anecdotes and misinformation to systematic science." J Psychopharmacol. Mar. 2022; 36(3): 258-272.
Sizemore et al., "Serotonergic Modulation Across Sensory Modalities." J Neurophysiol. Jun. 1, 2020;123(6):2406-2425. doi: 10.1152/jn.00034.2020. Epub May 13, 2020.
Timmermann, Christopher et al. "Neural correlates of the DMT experience assessed with multivariate EEG." Sci Rep. Nov. 19, 2019;9(1):16324. 13 pages.
University of Zurich. Compositions and kits comprising N,N-dimethyltryptamine and harmine and their use in therapy. European Patent Application Serial No. EP20181489, filing date Jun. 24, 2020, receipt by WIPO Jul. 6, 2021. 56 pages.
U.S. Appl. No. 19/173,537, filed Apr. 8, 2025, by Witowski et al.
U.S. Appl. No. 19/258,381, filed Jul. 2, 2025, by Fawaz et al.
Acasta Gneiss, "information on IV/IM HCI doses needed." 5 Hive forums.5meodmt.org, [Online] (Sep. 11, 2017); Retrieved from Internet Archive Wayback Machine at: [https://web.archive.org/web/20240108165249/https://forums.5meodmt.org/index.php/topic,50525.msg54571.html#msg54571] on [Oct. 27, 2025]; 5 pages.
Acosta-Urquidi, "EEG studies of the acute effects of 5-MeO-DMT." World Bufo Alvarius Conference, Mexico, Jul. 27-29, 2018, presentation, 31 pages.
Aghajanian, G K, "LSD and 2-bromo-LSD: comparison on effects on serotonergic neurones and on neurones in two serotonergic projection areas, the ventral lateral geniculate and amygdala." Neuropharmacology. Sep. 1976;15(9):521-8. doi: 10.1016/0028-3908(76)90102-7.
Agurell et al., "Alkaloid Content of Banisteriopsis Rusbyana." American Journal of Pharmacy and the Sciences Supporting Public Health. Sep.-Oct. 1968; 140(5):148-51.
Alexander et al., "Preclinical models for evaluating psychedelics in the treatment of major depressive disorder." Br J Pharmacol. Oct. 28, 2024. doi: 10.1111/bph.17370, 22 pages.
American Journal of Managed Care, "Dr. Michael Thase on the Prevalence of Stigma Surrounding Major Depressive Disorder," [Online] American Journal of Managed Care (AJMC) Psych Congress Conference Video, (Nov. 19, 2018) [retrieved on unknown date from the Internet at: https://www.ajmc.com/view/dr-michael-thase-on-the-prevalence-of-stigma-surrounding-major-depressive-disorder]; 6 pages.
Anonymous, "Self served Bufo and set my soul free," Reveddit.com, comment in forum post, [Online] (Sep. 2019); [Retrieved from the internet on Oct. 27, 2025, from URL: https://www.reveddit.com/v/5MeODMT/comments/daiff3/self_served_bufo_and_set_my_soul_free/f1pwdof/?utm_source=share&utm_medium=web2x&context=3]; 2 pages.
Anonymous, "The God Molecule." Reddit, forum post comment, [Online] (Nov. 17, 2019) [retrieved from the internet on Nov. 24,

(56) References Cited

OTHER PUBLICATIONS 2025, at URL: https://www.reveddit.com/v/5MeODMT/comments/dxtdcx/the_god_molecule/f7w0yi7/?utm_source=share&utm_medium=web2x&context=3]; 1 page.
Anonymous, "The Sonoran Desert Toad, *Bufo alvarius*." EROWID.org, [Online] (Oct. 18, 2017); retrieved from Internet Archive Wayback Machine at URL: [https://web.archive.org/web/20171018062456/http://www.erowid.org:80/archive/sonoran_desert_toad/5meo.htm] on [Oct. 1, 2025]; 5 pages.
APA, "Diagnostic and Statistical Manual of Mental Disorders, Fifth Edition, DSM-5." American Psychiatric Association, Jun. 2013, p. 5-15, 19-25, 155-188, 271-281, 36 pages.
APA, "What Is Depression?" [Online] (2018, month unknown), Retrieved from Internet Archive Wayback Machine at: [https://web.archive.org/web/20190117034902/https://www.psychiatry.org/patients-families/depression/what-is-depression] on [Jan. 17, 2019]; 4 pages.
Araujo et al., "The hallucinogenic world of tryptamines: an updated review." Arch Toxicol. Aug. 2015; 89(8): 1151-73.
Australian and New Zealand Clinical Trials Registry, Identifier ACTRN12622000851763. "A phase 1, First-in-Human, open-label, Safety, Tolerability and Pharmacokinetic Study of Single-Ascending Doses of VLS-01 in Healthy Adult Volunteers." [Internet]: Sydney (NSW): NHMRC Clinical Trials Centre, University of Sydney Australia; (Jun. 16, 2022); last updated Nov. 14, 2022. [Retrieved from the Internet Oct. 24, 2025, from https://www.anzctr.org.au/Trial/Registration/TrialReview.aspx?id=383956&isReview=true]; 6 pages.
Australian and New Zealand Clinical Trials Registry, Identifier ACTRN12624000025538. "A Phase 1b, Single-Centre, Open-Label Dose Ranging Study of an Optimized Formulation of VLS-01 in Healthy Adult Volunteers." [Internet]: Sydney (NSW): NHMRC Clinical Trials Centre, University of Sydney Australia; (Jan. 12, 2024); last updated Oct. 6, 2025. [Retrieved from the Internet Oct. 24, 2025 from https://www.anzctr.org.au/Trial/Registration/TrialReview.aspx?id=386607&isReview=true]; 6 pages.
Australian and New Zealand Clinical Trials Registry, Identifier NCT06524830. "A Phase 2, Multicenter, Double-blind, Randomized, Placebo-controlled Trial to Assess the Efficacy, Safety, and Tolerability of Repeated Doses of VLS-01 Buccal Film in Participants With Treatment Resistant Depression." [Internet]: Sydney (NSW): NHMRC Clinical Trials Centre, University of Sydney Australia; (Jul. 29, 2024); last updated Oct. 2, 2025. [Retrieved from the Internet Oct. 24, 2025, from https://www.anzctr.org.au/Trial/Registration/TrialReview.aspx?id=24321&isClinicalTrial=True]; 6 pages.
Barrett (2017) "The Challenging Experience Questionnaire: Characterization of challenging experiences with psilocybin mushrooms." J Psychopharmacol. Dec. 2016;30(12):1279-1295. doi: 10.1177/0269881116678781. Epub Nov. 17, 2016.
Barrett et al., "Qualitative and Quantitative Features of Music Reported to Support Peak Mystical Experiences during Psychedelic Therapy Sessions." Front Psychol. Jul. 25, 2017:8:1238. doi: 10.3389/fpsyg.2017.01238. eCollection 2017, 12 pages.
Barrett et al. "Validation of the revised Mystical Experience Questionnaire in experimental sessions with psilocybin." Journal of Psychopharmacology. Nov. 2015;29(11):1182-1190. doi: 10.1177/0269881115609019.
Baumeister et al. "Classical hallucinogens as antidepressants? A review of pharmacodynamics and putative clinical roles." Therapeutic Advances in Psychopharmacology. Aug. 2014;4(4):156-169. doi: 10.1177/2045125314527985.
Beliveau, et al., "A High-Resolution In Vivo Atlas of the Human Brain's Serotonin System," J Neurosci. Jan. 4, 2017; 37(1):120-128.
Belser, et al., "Patient Experiences of Psilocybin-Assisted Psychotherapy: An Interpretative Phenomenological Analysis," Journal of Humanistic Psychology Apr. 2017; vol. 57(4):354-388.
Biffhenderson, forum post in thread titled: "The Big & Dandy 5-MeO-DMT Thread—Second Launch." [Online] bluelight.org (May 2012) available at: [https://bluelight.org/xf/threads/the-big-dandy-5-meo-dmt-thread-second-launch.599032/post-10587079]; retrieved from Internet Archive Wayback Machine at URL: [https://web.archive.org/web/20240120193627/https://bluelight.org/xf/threads/the-big-dandy-5-meo-dmt-thread-second-launch.599032/page-2#post-10587079] on [Sep. 30, 2025]; 2 pages.
Birnbaum et al., "Employer burden of mild, moderate, and severe major depressive disorder: mental health services utilization and costs, and work performance." Depress Anxiety. (2010, month unknown); 27(1):78-89. doi: 10.1002/da.20580, Epub Jun. 30, 2009.
Blinny, "Cranial Chomping 5-MeO-DMT," [Online] Erowid Experience Vaults, (Aug. 29, 2003); Retrieved from Internet Archive Wayback Machine at URL: [https://web.archive.org/web/20070607053411/https://erowid.org/experiences/exp.php?ID=26469 on [Oct. 1, 2025]; 2 pages.
Breaking Convention, "Rafael Lancelotta—5-MeO-DMT Use in the Global Population." [Video] Youtube.com, posted (Sep. 2019); available at: https://www.youtube.com/watch?v=7GSsqoKj0Vs] (accessed Sep. 30, 2025); 1 page.
Canal CE. "Serotonergic psychedelics: experimental approaches for assessing mechanisms of action." In New Psychoactive Substances: Pharmacology, Clinical, Forensic and Analytical Toxicology, Springer International Publishing. Mar. 13, 2018; 227-260.
Canal et al. "Head-twitch response in rodents induced by the hallucinogen 2, 5dimethoxy4iodoamphetamine: a comprehensive history, a reevaluation of mechanisms, and its utility as a model." Drug Test Anal. Apr. 19, 2012;4(0):556-576. doi: 10.1002/dta.1333.
Carhart-Harris, et al., "LSD enhances suggestibility in healthy volunteers." Psychopharmacology (Berl). Feb. 2015;232(4):785-94. Epub Sep. 23, 2014, 10 pages.
Carhart-Harris, et al., "Psilocybin with psychological support for treatment-resistant depression: an open-label feasibility study," Lancet Psychiatry. Jul. 2016; 3(7):619-27. Epub May 17, 2016.
Carhart-Harris et al. "Psilocybin with psychological support for treatment-resistant depression: six-month follow-up." Psychopharmacology. 235(2):399-408 (Feb. 2018). doi: 10.1007/s00213-017-4771-x.
Carpenter, David E., "5-MeO-DMT: The 20-Minute Psychoactive Toad Experience That's Transforming Lives," Forbes.com [Online] (Feb. 2, 2020) updated Dec. 10, 2021, [retrieved on Sep. 30, 2025, from the Internet at: https://www.forbes.com/sites/davidcarpenter/2020/02/02/5-meo-dmt-the-20-minute-psychoactive-toad-experience-thats-transforming-lives/?sh=3b79337838a1]; 11 pages.
Chaosbydesign, "A Blissful Peace of Mind, Buprenorphine & 5-MeO-DMT." Erowid.org, [Online] (Sep. 29, 2017), Retrieved from Internet Archive Wayback Machine at URL: [URL: https://web.archive.org/web/20170929165328/https://erowid.org/experiences/exp.php?ID=83974] on [Sep. 29, 2025]; 3 pages.
Clinical trial application form for clinical trial GH001-MDD-102, pp. 1 and 19, dated Oct. 20, 2020, 2 pages.
Clinical trial application form for clinical trial GH001-MDD-102, pp. 1 and 19, dated Jun. 3, 2019, 2 pages.
Cowen, "Altered states: psilocybin for treatment-resistant depression." Lancet Psychiatry. Jul. 2016;3(7):592-3. doi: 10.1016/S2215-0366(16)30087-6. Epub May 17, 2016.
Dameron, Emerson, "Mr. Toad's Wild Ride: 4 Seasons in 30 Minutes on 5-MeO-DMT." Medium, [Online] (May 25, 2017) [Retrieved on Jan. 28, 2024, from Internet Archive at: https://archive.ph/LHIDV]; 5 pages.
Davis, AK, "The healing potential of 5-MeO-DMT: Results from two survey studies." Abstract of a presentation given in Apr. 2018 at the Midwest Psychedelic Therapy Symposium, Madison Wisconsin, 2 pages.
Davis, et al., "5-Methoxy-N, N-Dimethyltryptamine (5-MeO-DMT): Patterns of use, motives for consumption, and acute subjective effects." Poster given at the 12th Annual Bayview Research Symposium, Johns Hopkins University School of Medicine, Baltimore, MD. Dec. 2017, 10.13140/RG.2.2.32653.84960, 2 pages.
Dean, et al., "Indolethylamine-N-methyltransferase Polymorphisms: Genetic and Biochemical Approaches for Study of Endogenous N,N,-dimethyltryptamine." Front Neurosci. Apr. 23, 2018:12:232. doi: 10.3389/fnins.2018.00232. eCollection 2018, 16 pages.
Declaration and CV of Dr. Michael Thase, dated May 22, 2025, submitted in Opposition proceedings of EP Patent No. 3927337, 121 pages.

(56) References Cited

OTHER PUBLICATIONS

Declaration of Dr. Mark Seelig Jul. 7, 2025, filed in European Opposition proceedings against EP3927337, 3 pages.
Declaration of Dr. Mark Seelig Nov. 13, 2024, filed in European Opposition proceedings against EP3927337, 3 pages.
Demyttenaere, et al., "The Impact of (the Concept of) Treatment-Resistant Depression: An Opinion Review," Int J Neuropsychopharmacol. Feb. 1, 2019; 22(2):85-92.
Dos Santos et al., "Long-term effects of ayahuasca in patients with recurrent depression: a 5-year qualitative follow-up." Archives of Clinical Psychiatry. 45(1):22-24. Jan.-Feb. 2018. https://doi.org/10.1590/0101-60830000000149.
Emo Earache, "Friday Night Alone in the Universe." [Online] Erowid.org, (Oct. 21, 2006); [Retrieved Sep. 29, 2025, from the internet at URL: https://www.erowid.org/experiences/exp.php?ID=56696]; 6 pages.
Entheohealing, "Interplay between psychotherapy and psychedelics." [Online] Reddit, (Jun. 30, 2018); [retrieved from the internet on Sep. 30, 2025 from URL: https://www.reddit.com/r/TripTherapy/comments/8v5c4f/interplay_between_psychotherapy_and_psychedelics/]; 6 pages.
Entheohealing, "The Nuclear Option: A Personal Story of Treating Social Anxiety with 5-MeO-DMT Psychedelic Therapy." [Online] Reddit, (Jun. 2018), [retrieved Sep. 30, 2025 from the internet at URL: https://www.reddit.com/r/TripTherapy/comments/8zdhxg/the_nuclear_option_a_personal_story_of_treating/]; 5 pages.
EP Application No. 19158774.0, filed Feb. 22, 2019; inventor Terwey; Theis; 45 pages.
EP Application No. 20200710059, Third Party Observation submitted Jan. 19, 2024; Applicant/Proprietor GH Research Ireland Limited; 3 pages.
EP Application No. 20710059.5, communication in Opposition proceedings dated Dec. 3, 2024; Applicant GH Research Ireland Limited; 35 pages.
EP Application No. 20710059.5, communication in Opposition proceedings dated Jul. 15, 2025; Applicant GH Research Ireland Limited; 10 pages.
EP Application No. 20710059.5, communication in Opposition proceedings dated Jun. 10, 2025; Applicant GH Research Ireland Limited; 127 pages.
EP Application No. 20710059.5, communication in Opposition proceedings dated Sep. 9, 2025; Applicant GH Research Ireland Limited; 23 pages.
EP Application No. 20710059.5, Third Party Observation dated Oct. 26, 2023, Applicant/proprietor GH Research Ireland Limited; 31 pages.
EP Application No. 20710060.3, Communication under Article 94(3) dated Dec. 16, 2022; Applicant GH Research Ireland Limited 14 pages.
EP Application No. 22917527.8, Extended European Search Report mailed Oct. 31, 2025; Applicant ATAI Therapeutics, Inc.; 8 pages.
EP Patent No. 3927337, Notice of opposition dated May 22, 2024, Applicant GH Research Ireland Limited; 21 pages.
EP Patent No. 3927337, Notice of opposition dated Nov. 19, 2024; Applicant GH Research Ireland Limited; 58 pages.
EP Patent No. 3927337, Reply from Opponent in opposition proceedings, filed Jul. 9, 2025; Applicant GH Research Ireland Limited; 9 pages.
EP Patent No. 3927337, Reply of the patent proprietor in Opposition proceedings, dated Jun. 3, 2025; Applicant GH Research Ireland Limited; 126 pages.
Erowid, "5-MeO-DMT Dosage." [Online] EROWID.org (Feb. 14, 1999); Modified Jan. 1, 2000, Retrieved from Internet Archive Wayback Machine at URL: [https://web.archive.org/web/20000407105145/https://erowid.org/chemicals/5meo_dmt/5meo_dmt_dose.shtml] on [Oct. 1, 2025]; 1 page.
Erowid Crew Blog, "Intractable Byproduct in 5-MeO-DMT Samples." [Online] Erowid.org (Aug. 3, 2021); [retrieved Oct. 1, 2025, from https://www.erowid.org/columns/crew/2021/08/5-meo-dmt_synthesis_byproduct/]; 4 pages.
Euda, "The drug situation in Europe up to 2023—an overview and assessment of emerging threats and new developments." European Union Drugs Agency, European Drug Report 2023, last updated Jun. 16, 2023, 16 pages.
EudraCT & EU CTR Question and Answer table, Frequently Asked Questions & Answers (FAQs)—V1.3 (Mar. 2019), 32 pages.
European Medicines Agency, EudraCT & EU CTR Frequently Asked Questions, V.2.5, Jan. 31, 2025, 30 pages.
European Union Clinical Trials Register, EudraCT No. 2018-004208-20, "A phase 1/2 study of GH001 in patients with treatment-resistant depression." (Jul. 1, 2019); [retrieved from the internet on Sep. 10, 2024, from https://www.clinicaltrialsregister.eu/ctr-search/trial/2018-004208-20/NL]; 5 pages.
Ewing, Christopher G., "Ground to Source—Experiencing the Divine Within." Thepracticaltripper.wordpress.com, [Online] (Apr. 15, 2017) [retrieved on Sep. 30, 2025, from the Internet at: https://thepracticaltripper.wordpress.com/2017/04/15/ground-to-source-experiencing-the-divine-within-2/]; 10 pages.
Fabbri et al., "The Genetics of Treatment-Resistant Depression: A Critical Review and Future Perspectives." Int J Neuropsychopharmacol. Feb. 1, 2019;22(2):93-104. doi: 10.1093/ijnp/pyy024.
Filip.Zaruba, "introduction of me andy my 5-MeO movie." [Online] 5 Hive forums.5meodmt.org, (May 31, 2018); Retrieved from Internet Archive Wayback Machine at: [https://web.archive.org/web/20231122183352/https://forums.5meodmt.org/index.php/topic,50738.msg55435.html#msg55435] on [Oct. 27, 2025]; 2 pages.
Form F-1 (Registration Statement Under Securities Act 1933) filed by GH Research PLC (of which GH Research is a subsidiary) with the Securities and Exchange Commission on Jun. 21, 2021, 248 pages.
Garcia, Isra, "Bufo Alvarius Toad / 5MeO-DMT—the awakening." [Online] (Jan. 28, 2019), [retrieved on Sep. 30, 2025, from the Internet at: https://isragarcia.com/bufo-alvarius-toad-5meo-dmt-awakening]; 9 pages.
Garcia-Romeu et al. "Psilocybin-occasioned mystical experiences in the treatment of tobacco addiction." Current Drug Abuse. Reviews. Dec. 2014;7(3):157-164. doi: 10.2174/1874473708666150107121331.
GH Reasearch, "GH Research Announces Closing of $125 Million Oversubscribed Series B Financing." Press-release, Apr. 12, 2021, 1 page.
GH Research Announces Appointment of Dr. Velichka "Villy" Valcheva of Chief Executive Officer, Press-release dated Sep. 3, 2024, 1 page.
GH Research, Corporate Presentation, Mar. 2022, 15 pages.
GH Research, Corporate Presentation, Mar. 2023, 30 pages.
GH Research, Corporate Presentation, May 2022, 28 pages.
GH Research, Corporate Presentation, May 2023, 30 pages.
GH Research, Corporate Presentation, Nov. 2022, 28 pages.
GH Research (year: 2025, month: unknown), data for Spravato (esketamine), 3 pages.
Goodwin et al., "Single-Dose Psilocybin for a Treatment-Resistant Episode of Major Depression." N Engl J Med. Nov. 3, 2022;387(18):1637-1648. doi: 10.1056/NEJMoa2206443.
Goodwin et al., "Supplementary Appendix to Single-Dose Psilocybin for a Treatment-Resistant Episode of Major Depression." Supplementary Appendix; N Engl J Med. Nov. 3, 2022;387(18):1637-1648, 249 pages.
Greatmoosey, "Update: 30 days after my 5meoDMT experience." [Online] Reddit, (Oct. 27, 2019); [retrieved from the Internet on Sep. 30, 2025, at: https://www.reddit.com/r/Psychonaut/comments/dnup28/update_30_days_after_my_5meodmt_experience/]; 5 pages.
Gumpper, Ryan, H. et al., "The structural diversity of psychedelic drug actions revealed," Nat Commun. Mar. 19, 2025;16(1):2734. doi: 10.1038/s41467-025-57956-7, 13 pages.
Halberstadt et al., "Behavioral effects of „,-tetradeutero-5-MeO-DMT in rats: comparison with 5-MeO-DMT administered in combination with a monoamine oxidase inhibitor," Psychopharmacology (Berl). Jun. 2012;221(4):709-18. doi: 10.1007/s00213-011-2616-6. Epub Jan. 6, 2012.
Halberstadt et al., "Modification of the effects of 5-methoxy-N,N-dimethyltryptamine on exploratory behavior in rats by monoamine oxidase inhibitors." Psychopharmacology (Berl). Nov. 2008;201(1):55-66. doi: 10.1007/s00213-008-1247-z. Epub Jul. 8, 2008.

(56) References Cited

OTHER PUBLICATIONS

Handshake, "Toads Poison Use Is Not An Ancient Indigneous Tradition." 5 Hive forums.5meodmt.org, [Online] (Nov. 30, 2017); Retrieved from Internet Archive Wayback Machine at: [https://web.archive.org/web/20231122182449/https://forums.5meodmt.org/index.php /topic,50611.msg54941.html#msg54941] on [Oct. 27, 2025]; 6 pages.
Harbonic_Older, "Journey to the Center of the Onion, 5-MeO-DMT." Erowid.org, [Online] (Nov. 1, 2004); Retrieved from Internet Archive Wayback Machine at URL: [https://web.archive.org/web/20130209080256/https://www.erowid.org/experiences/exp.php?ID=34918] on [Sep. 29, 2025]; 2 pages.
Hassan et al., "A Review on the Pharmacological and Traditional Properties of Mimosa Pudica." International Journal of Pharmacy and Pharmaceutical Sciences (Mar. 2019) 11(3), 12-16.
Hermann, "Psychiatric Comorbidity in Chronic Epilepsy: Identification, Consequences, and Treatment of Major Depression" Epilepsia. (Aug. 2, 2005), 2000:41 Suppl 2:S31-41. doi: 10.1111/j.1528-1157.2000.tb01522.x.
Herrmann, "The Sunnybrook Stroke Study: A Prospective Study of Depressive Symptoms and Functional Outcome." Stroke. (Mar. 1, 1998); 29: 618-624.
Hesselink, et. al, "Transformative Psychopharmacology: the Case of 5-Methoxy-N,N-Dimethyltryptamine." International Journal of Psychotherapy Practice and Research, (Jan. 2019), 1(3), 9-15.
Holtzheimer, et al., "Deep Brain Stimulation for Treatment-Resistant Depression," Clinical Case Conference from the Emory University School of Medicine, Am J Psychiatry, Dec. 2010; 167:12, pp. 1437-1444.
Innerexplorer, "Defining Intramuscular Dosage Range, 5-MeO-DMT." [Online] Erowid.org (Jan. 2, 2017); [retrieved Sep. 29, 2025, from the internet at URL: https://www.erowid.org/experiences/exp.php?ID=109250]; 3 pages.
Jabberwocky, forum post in thread titled "Euphorigenic, entactogenic, non-toxic, non-hallucinogenic tryptamine(s)?" bluelight.org [Online] (Mar. 10, 2009) Available at: [https://bluelight.org/xf/threads/euphorigenic-entactogenic-non-toxic-non-hallucinogenic-tryptamine-s.423423/post-6922410]; Retrieved from Internet Archive Wayback Machine at URL: [https://web.archive.org/web/20240121145750/https://bluelight.org/xf/threads/euphorigenic-entactogenic-non-toxic-non-hallucinogenic-tryptamine-s.423423/#post-6922410] on [Oct. 27, 2025]; 10 pages.
Jacob, et al. "Structure-activity relationships of classic hallucinogens and their analogs." NIDA Research Monograph, (Year: 1994, month: unknown), 19 pages.
Jaffe et al., "The humanistic and economic burden of treatment-resistant depression in Europe: a cross-sectional study." BMC Psychiatry. Aug. 7, 2019;19(1):247. doi: 10.1186/s12888-019-2222-4.
Johns Hopkins Medicine, "Fast-Acting Psychedelic Associated With Improvements In Depression/Anxiety." [Online] Johns Hopkins Medicine News & Publications Newsroom, (Mar. 18, 2019); [retrieved on Sep. 30, 2025, from the Internet at: https://www.hopkinsmedicine.org/news/newsroom/news-releases/2019/03/fast-acting-psychedelic-associated-with-improvements-in-depressionanxiety]; 3 pages.
Johnson&Johnson, "Janssen Announces U.S. FDA Approval of Spravato (esketamine) CIII Nasal Spray for Adults with Treatment-Resistant Depression (TRD) Who Have Cycled Through Multiple Treatments Without Relief," Johnson & Johnson press release, Mar. 5, 2019, 11 pages.
Johnson&Johnson, "Janssen Announces U.S. FDA Approval of Spravato (esketamine) CIII Nasal Spray to Treat Depressive Symptoms in Adults with Major Depressive Disorder with Acute Suicidal Ideation or Behavior," Johnson & Johnson press release, Aug. 3, 2020, 13 pages.
Johnson&Johnson, "Spravato (esketamine) approved in the U.S. as the first and only monotherapy for adults with treatment-resistant depression," Johnson & Johnson press release, Jan. 21, 2025,10 pages.
Kaelen et al., "The hidden therapist: evidence for a central role of music in psychedelic therapy." Psychopharmacology (Berl). Feb. 2018;235(2):505-519. doi: 10.1007/s00213-017-4820-5. Epub Feb. 2, 2018.
Karst, Matthias et al., "The non-hallucinogen 2-bromo-lysergic acid diethylamide as preventative treatment for cluster headache: an open, non-randomized case series." Cephalalgia. Sep. 2010;30(9):1140-4. doi: 10.1177/0333102410363490. Epub Mar. 26, 2010.
Kaufman, et al., "The 5-HT1A receptor in Major Depressive Disorder." Eur Neuropsychopharmacol. Mar. 2016; 26(3):397-410. doi:10.1016/j.euroneuro.2015.12.039. Epub Jan. 11, 2016.
Kennett, et al., "Single administration of 5-HT1A agonists decreases 5-HT1A presynaptic, but not postsynaptic receptor-mediated responses: relationship to antidepressant-like action." Eur J Pharmacol. Jun. 12, 1987;138(1):53-60.
Lawlor, Sean, "5-MeO-DMT: Light and Shadow in the Psychedelic Toad." [Online] Psychedelic Times, (Nov. 20, 2019), [retrieved from the Internet Sep. 30, 2025, at: https://psychedelictimes.com/5-meo-dmt-psychedelic-toad/]; 16 pages.
Lawrence et al., "Sports Medicine, Mental Health & Well-Being, and Psychedelics." [Online] British Journal of Sports Medicine (Nov. 28, 2019) [retrieved from internet Sep. 29, 2025, from https://blogs.bmj.com/bjsm/2019/11/28/sports-medicine-mental-health-well-being-and-psychedelics/]; 14 pages.
Lewis et al., "Two dose investigation of the 5-HT-agonist psilocybin on relative and global cerebral blood flow." Neuroimage. Oct. 1, 2017:159:70-78. doi: 10.1016/j.neuroimage.2017.07.020. Epub Jul. 12, 2017.
Lewis, V., et al., "A non-hallucinogenic LSD analog with therapeutic potential for mood disorders." Cell Rep. Mar. 28, 2023;42(3):112203. doi: 10.1016/j.celrep.2023.112203. Epub Mar. 6, 2023. 27 pages.
Liechti, "Modern Clinical Research on LSD." Neuropsychopharmacology. Oct. 2017;42(11):2114-2127. doi: 10.1038/npp.2017.86. Epub Apr. 27, 2017.
Llado-Pelfort, et al., "Effects of Hallucinogens on Neuronal Activity." Curr Top Behav Neurosci. 2018: 36:75-105. doi: 10.1007/7854_2017_473. Epub Feb. 26, 2017, 31 pages.
Majic, "Peak experiences and the afterglow phenomenon: When and how do therapeutic effects of hallucinogens depend on psychedelic experiences?" Journal of Psychopharmacology. 29(3):241-253 (Feb. 9, 2015).
Malhi et al., "Treatment-resistant depression: problematic illness or a problem in our approach?" Br J Psychiatry. Jan. 2019;214(1): 1-3. doi: 10.1192/bjp.2018.246.
Marek et al., "Evidence for involvement of 5-hydroxytryptamine1 receptors in antidepressant-like drug effects on differential-reinforcement-of-low-rate 72-second behavior." J Pharmacol Exp Ther. Jul. 1989; 250(1):60-71.
Mcilhenny, et al., "Ayahuasca characterization, metabolism in humans, and relevance to endogenous N,N-dimethyltryptamines." Doctoral dissertation, (Aug. 2012), Louisiana State University and Agricultural and Mechanical College. Available from LSU Digital Commons. (No. 2049), 215 pages.
Mckenna, et al., "Monoamine oxidase inhibitors in South American hallucinogenic plants: tryptamine and beta-carboline constituents of ayahuasca." Journal of Ethnopharmacology. Apr. 1984;10(2):195-223. doi: 10.1016/0378-8741(84)90003-5.
Meccia et al., "Treatment of major depressive disorder and treatment resistant depression with 5-MeO-DMT: impact of 25 years of non-traditional public scientific communication and education on clinical development and commercialization." Porta Sophia, Madison, WI USA (Nov. 12, 2024), 15 pages.
Milliere et al., "Psychedelics, Meditation, and Self-Consciousness." Front Psychol. Sep. 4, 2018:9:1475. doi: 10.3389/fpsyg.2018.01475. eCollection 2018, 29 pages.
Mohebbi (2018) "Patient centric measures for a patient centric era: Agreement and convergent between ratings on The Patient Global Impression of Improvement (PGI-I) scale and the Clinical Global Impressions Improvement (CGI-S) scale in bipolar and major depressive disorder" Eur Psychiatry. Sep. 2018:53:17-22. doi: 10.1016/j.eurpsy.2018.05.006. Epub May 30, 2018.

(56) References Cited

OTHER PUBLICATIONS

Mukherjee, Pranoy, "How can I overcome (existential) depression?" [Online] Quora forum response, (Jan. 27, 2018) Retrieved from Internet Archive at URL: [https://archive.ph/7PThx] on [Oct. 27, 2025]; 2 pages.
Muller (2003) "Differentiating moderate and severe depression using the Montgomery-Asberg depression rating scale (MADRS)" J Affect Disord. Dec. 2003;77(3):255-60. doi: 10.1016/s0165-0327(02)00120-9.
National Institutes of Health, "Depression Screening," [Online] (NIH)/National Library of Medicine, U.S. Dept. of Health & Human Services, (Dec. 15, 2022); [retrieved from the Internet on unknown date from: https://medlineplus.gov/lab-tests/depression-screening/]; 7 pages.
Null24, "N,N-DMT and it's connection to spiritual consciousness (or something like that)," dmt.nexus.me [Online] (Feb. 7, 2014); Retrieved from Internet Archive Wayback Machine at URL: [https://web.archive.org/web/20240108174403/https://www.dmt-nexus.me/forum/default.aspx?g=posts&m=520577#post520577] on [Jan. 8, 2024]; 4 pages.
Olin et al., "Mortality and Suicide Risk in Treatment-Resistant Depression: An Observational Study of the Long-Term Impact of Intervention." PLoS One. Oct. 2012; 7(10):e48002. doi: 10.1371/journal.pone.0048002. Epub Oct. 25, 2012, 11 pages.
Osorio et al., "Antidepressant effects of a single dose of ayahuasca in patients with recurrent depression: a preliminary report." Braz J Psychiatry. Jan.-Mar. 2015;37(1):13-20. doi: 10.1590/1516-4446-2014-1496.
Palhano-Fontes et al., "A randomized placebo-controlled trial on the antidepressant effects of the psychedelic ayahuasca in treatment-resistant depression." bioRxiv preprint doi: https://doi.org/10.1101/103531, Aug. 15, 2017, 10 pages.
Palhano-Fontes et al., "Rapid antidepressant effects of the psychedelic ayahuasca in treatment-resistant depression: a randomized placebo-controlled trial." Psychol Med. Mar. 2019;49(4):655-663. doi: 10.1017/S0033291718001356. Epub Jun. 15, 2018.
PCT Application No. PCT/US2025/039639, Invitation to Pay Additional Fees mailed Oct. 27, 2025, Applicant ATAI Therapeutics, Inc.; 2 pages.
Polanco, Martin, "Psychedelic therapy with 5MeO-DMT." [Online] Martinpolancomd.com, (Jan. 3, 2020); retrieved from Internet Archive Wayback Machine at URL: [https://web.archive.org/web/20240216113910/https://www.martinpolancomd.com/post/psychedelic-therapy-with-5meo-dmt] on [Oct. 27, 2025]; 2 pages.
Porta Sophia, "Porta Sophia Publishes Narrative Review Manuscript Summarizing Historical Evidence of 5-MeO-DMT as a Compound Used in Therapeutic Practice." Press release, Nov. 12, 2024, 2 pages.
Porter, MD, et al., "The Merck Manual of Diagnosis and Therapy," Twentieth Edition, Merck Sharp & Dohme Corp., (Apr. 2018), pp. 1757-1761.
Psychedelics Today, "Rafael Lancelotta—Exploring 5-MeO-DMT." [Video] YouTube.com, posted (May 10, 2018). Available at: https://www.youtube.com/watch?v=kEp-Az9ibLM], (accessed Sep. 30, 2025), 1 page.
Qi et al., "The Development of Toad Toxins as Potential Therapeutic Agents." Toxins (Basel). Aug. 20, 2018;10(8):336. doi: 10.3390/toxins10080336, 14 pages.
Queensland Brain Institute, "Deep brain stimulation for depression hits a(nother) roadblock," [Online] The University of Queensland, (Aug. 20, 2015); last updated May 18, 2017, [retrieved from the internet on unknown date from: https://qbi.uq.edu.au/blog/2017/02/deep-brain-stimulation-depression-hits-another-roadblock]; 4 pages.
Quilty et al., "The structure of the Montgomery-sberg depression rating scale over the course of treatment for depression." Int J Methods Psychiatr Res. Sep. 2013;22(3):175-84. doi: 10.1002/mpr.1388. Epub Aug. 19, 2013.
Rakofsky, et al., "The prevalence and severity of depressive symptoms along the spectrum of unipolar depressive disorders: a post hoc analysis," J Clin Psychiatry. Nov. 2013; 74(11):1084-91.
Ramaekers, et al., "Regarding the clinical study with ref GH001-MDD-102 / NL70411.068.19 / METC 19-036." Letter to the CCMO, concerning clinical trial GH001-MDD-102, Oct. 13, 2020, 3 pages.
Raskin, Jonathan D., "Are There Viable Alternatives to DSM-5? Can ICD, PDM, HiTOP, RDOC, or PTMF win a kind of diagnostic game of thrones?," [Online] Psychology Today, (May 22, 2019) [retrieved from the Internet on Oct. 1, 2025 at: https://www.psychologytoday.com/us/blog/making-meaning/201905/are-there-viable-alternatives-to-the-dsm-5]; 15 pages.
Reckweg, et al., "A Phase 1, Dose-Ranging Study to Assess Safety and Psychoactive Effects of a Vaporized 5-Methoxy-N, N-Dimethyltryptamine Formulation (GH001) in Health Volunteers," Frontiers in Pharmacology, Nov. 2021; vol. 12, Article 760671, pp. 1-12.
Reckweg et al. "A phase 1/2 trial to assess safety and efficacy of a vaporized 5-methoxy-N,N-dimethyltryptamine formulation (GH001) in patients with treatment-resistant depression." Front Psychiatry. Jun. 20, 2023:14:1133414. doi: 10.3389/fpsyt.2023.1133414. eCollection 2023, 8 pages.
Retreat.Guru, "Dr. Gerardo Sandoval Isaac, About the teacher," [Online] Retreat.Guru, (publication date unknown); [retrieved Mar. 4, 2025, from https://retreat.guru/teachers/756-59/dr-g]; 3 pages.
Riga, et al., "The natural hallucinogen 5-MeO-DMT, component of Ayahuasca, disrupts cortical function in rats: reversal by antipsychotic drugs." Int J Neuropsychopharmacol. Aug. 2014;17(8):1269-82. doi: 10.1017/S1461145714000261. Epub Mar. 20, 2014.
Riga, et al., "The serotonin hallucinogen 5-MeO-DMT alters cortico-thalamic activity in freely moving mice: Regionally-selective involvement of 5-HT1A and 5-HT2A receptors." Neuropharmacology. Nov. 2018;142:219-230.
Rivier L., et al., "Ayahuasca," the South American hallucinogenic drink: An ethnobotanical and chemical investigation. Economic Botany 26, (Apr. 1972). https://doi.org/10.1007/BF02860772, 101-129.
Roger R., (Feb. 26, 2016) "What is the difference between 5-MeO DMT and DMT? Choosing a DMT Therapy." Psychedelic Times online, Feb. 26, 2016, 5 pages.
Roseman et al. "Quality of acute psychedelic experience predicts therapeutic efficacy of psilocybin for treatment-resistant depression." Frontiers in Pharmacology. Jan. 2018.8:974, 10 pages. doi: 10.3389/fphar.2017.00974.
Schenberg (2017) "Translation and cultural adaptation of the States of Consciousness Questionnaire (SOCQ) and statistical validation of the Mystical Experience Questionnaire (MEQ30) in Brazilian Portuguese" Archives of Clinical Psychiatry. Jan. 26, 2017, 44(1):1-5.
Schifano et al., "New Psychoactive Substances (NPS), Psychedelic Experiences and Dissociation: Clinical and Clinical Pharmacological Issues." Current Addiction Reports. Jun. 2019, 6:140-152.
Schmid et al., "Serotonin, but not N-Methyltryptamines, activates the serotonin 2A receptor via a β-Arrestin2/Src/Akt signaling complex in vivo." The Journal of Neuroscience, Oct. 6, 2010, 30(40), 13513-13524.
Shaikh et al., "Medicinal Value of Mimosa Pudica as an Anxiolytic and Antidepressant: a Comprehensive Review." World Journal of Pharmacy and Pharmaceutical Sciences. Mar. 2016 5(3), 420-432, 14 pages.
Shen et al., "Nonlinear pharmacokinetics of 5-methoxy-N, Ndimethyltryptamine in mice." Drug Metab Dispos. Jul. 2011; 39(7): 1227-34. doi: 10.1124/dmd.111.039107. Epub Apr. 4, 2011.
Stafford, Peter. "Psychedelics Encyclopedia." Ronin, Third Edition, Jan. 12, 1993, 257 pages.
Studerus et al. "Psychometric evaluation of the altered states of consciousness rating scale (OAV)." PloS One. Aug. 2010;5(8):e12412, 19 pages. doi: 10.1371/journal.pone.0012412.
Sullenchoirboy, "Molecular Death for the Warrior, 5-MeO-DMT." [Online] Erowid.org, (Feb. 15, 2003); Retrieved from Internet Archive Wayback Machine at URL: [https://web.archive.org/web/20130110114001/https://erowid.org/experiences/exp.php?ID=21268] on [Oct. 27, 2025]; 2 pages.
Szabo et al., "Psychedelics and immunomodulation: novel approaches and therapeutic opportunities." Front Immunol. Jul. 14, 2015:6:358. doi: 10.3389/fimmu.2015.00358. eCollection 2015, 11 pages.

(56) References Cited

OTHER PUBLICATIONS

Thase et al., "Safety and Efficacy of GH001 in TRD: Results from a Phase 2b, Double-blind, Randomized Controlled Trial." Poster presented at the American Society of Clinical Psychopharmacology Annual Meeting, May 27-30, 2025, 1 page.

Thase et al., "Safety and Efficacy of GH001 in TRD: Results from a Phase 2b, Double-blind, Randomized Controlled Trial." Presentation at the American Society of Clinical Psychopharmacology Annual Meeting, May 27-30, 2025, 16 pages.

Thase, Michael E., "How Should Efficacy Be Evaluated in Randomized Clinical Trials of Treatments for Depression?," J Clin Psychiatry, Apr. 1, 1999; 60 (suppl 4), pp. 23-31.

Thase, Michael E., "Psychiatric and medical comorbidity as contributing factors in treatment-resistant depression," 31st International Symposium on Controversies in Psychiatry—Innovation in Mental Health—Barcelona, Spain, Apr. 10-11, 2025, 6 pages.

Thase, Michael E., "The multifactorial presentation of depression in acute care." J Clin Psychiatry. Oct. 15, 2013; 74 Suppl 2:3-8, 6 pages.

Thase, Michael E., "Using biomarkers to predict treatment response in major depressive disorder: evidence from past and present studies," Dialogues Clin Neurosci. Dec. 2014; 16(4):539-44.

Third Wave, "The Essential Guide to 5-MEO-DMT, (5-MEO, Five-methoxy, The Power, Toad venom)." [Online] Thethirdwave.co (publication date unknown); retrieved from Internet Archive Wayback Machine at URL: [https://web.archive.org/web/20181109024846/https://thethirdwave.co/psychedelics/5-meo-dmt/] on [Sep. 29, 2025]; 22 pages.

U.S. Appl. No. 18/675,614, Third Party Pre-Issuance Submission filed Oct. 16, 2024; Inventor Terwey, Theis, 12 pages.

U.S. Appl. No. 19/284,159, filed Jul. 29, 2025; Inventor Craig, Kevin et al.

U.S. Appl. No. 19/358,021, filed Oct. 14, 2025; by Witowski, Christopher G. et al.

U.S. Appl. No. 19/478,315, filed Oct. 24, 2025; inventor Gibbs, Alan et al.

Uthaug, et al., "The Ethical and Ecological Considerations of Inhaling Bufotoxins from Incilius Alvarius." [Online] Psychedelics Today, (Oct. 3, 2018); [retrieved from the internet on Sep. 29, 2025, from URL: https://psychedelicstoday.com/2018/10/03/ethics-ecology-bufotoxins/]; 20 pages.

Wordsworth, Richard, "LSD doesn't just treat mental illness, 'it could actually heal the brain.'" [Online] Wired.uk (Mar. 9, 2017) article, Retrieved from Internet Archive Wayback Machine at URL: [https://web.archive.org/web/20230510125630/https://www.wired.co.uk/article/khaliya-mental-health] on [Sep. 30, 2025]; 9 pages.

Yaesutom, forum post in thread titled: "The Big & Dandy 5-MeO-DMT Thread—First Launch." [Online] bluelight.org (Jan. 28, 2004); available at: [https://bluelight.org/xf/threads/the-big-dandy-5-meo-dmt-thread-first-launch.72085/post-1589648]; retrieved from Internet Archive Wayback Machine at URL: [https://web.archive.org/web/20240119092733/https://bluelight.org/xf/threads/the-big-dandy-5-meo-dmt-thread-first-launch.72085/page-5#post-1589648] on [Oct. 27, 2025]; 10 pages.

Yann, "Yann with Ayahuasca, My experience healing with Ayahuasca and other entheogens." [Online] Yannwithayahuasca.com (Sep. 19, 2017); Retrieved from Internet Archive Wayback Machine at URL: [https://web.archive.org/web/20211026092140/https://yannwithayahuasca.com/about/] on [Oct. 27, 2025]; 7 pages.

Yannwithayahuasca, "Can you Bad Trip on Bufo Alvarius / Sapito ? Against depression : Ayahuasca or Bufo Alvarius ?" [Video] Youtube.com, posted (May 25, 2017). Available at: [https://www.youtube.com/watch?v=4GcU2outMFs], (accessed Sep. 30, 2025), 3 pages.

Zagorski, Nick, "Experts Debate What's Next for DBS for Depression," Psychiatry Online, Clinical & Research, Psychiatric News, Mar. 2020; vol. 55, Issue 6, 4 pages.

Zomakmk7, "5-meo-dmt cured my depression," [Online] DMT.NEXUS.ME, (Nov. 14, 2018); Retrieved from Internet Archive Wayback Machine at URL: [https://web.archive.org/web/20240120142828/https://www.dmt-nexus.me/forum/default.aspx?g=posts&m=926667] on [Oct. 27, 2025]; 1 page.

* cited by examiner

DIMETHYLTRYPTAMINE ANALOGUES AS NITRIC OXIDE DELIVERY DRUGS

CROSS-REFERENCE TO RELATED APPLICATION

This application is a continuation of U.S. patent application Ser. No. 18/147,499, filed Dec. 28, 2022, now U.S. Pat. No. 12,012,381, which claims the benefit of priority to U.S. Provisional Application No. 63/295,199, filed Dec. 30, 2021, each of which is hereby incorporated by reference in their entirety.

BRIEF SUMMARY OF THE INVENTION

In embodiments, the present disclosure provides dimethyltryptamine derivatives that release nitric oxide (NO) in vivo.

In embodiments, the present disclosure provides prodrugs of dimethyltryptamine and derivatives thereof.

In embodiments, the present disclosure provides compounds of Formula (I), Formula (II), or pharmaceutically acceptable salts thereof.

In embodiments, the present disclosure provides a compound of Formula (I):

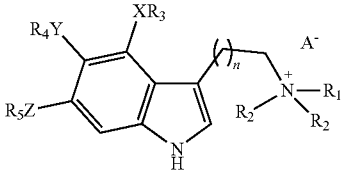

or a pharmaceutically acceptable salt thereof; wherein, $R_1$, $R_3$, $R_4$ and $R_5$ are independently H, halogen, $C_1$-$C_6$ alkyl, —(C═O)$(CR_7R_7')_n$—$ONO_2$, or —(C═O)$(CR_7R_7')_m$—$CH(NH_2)CH_2ONO_2$;

each $R_2$ is independently $C_1$-$C_6$ alkyl;

X, Y, and Z are independently absent, H, O, S, NH and —O—(P═O)OHO—;

$R_7$ and $R_7'$ are independently H, halogen, or $C_1$-$C_6$ alkyl;

m is 2, 3, or 4;

each n is independently 1, 2, 3, 4 or 5; and $A^-$ is a pharmaceutically acceptable anion, wherein at least one of $R_1$, $R_3$, $R_4$ and $R_5$ are —(C═O)$(CR_7R_7')_n$—$ONO_2$ or —(C═O)$(CR_7R_7')_m$—$CH(NH_2)CH_2ONO_2$.

In embodiments, the present disclosure provides a compound of Formula (II):

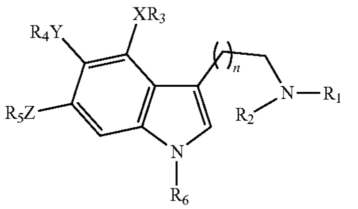

or a pharmaceutically acceptable salt thereof; wherein, $R_3$, $R_4$, and $R_5$ are independently H, halogen, $C_1$-$C_6$ alkyl, —(C═O)$(CR_7R_7')_n$—$ONO_2$, —(C═O)$(CR_7R_7')_m$—$CH(NH_2)CH_2ONO_2$;

$R_1$ and $R_6$ are independently H, $C_1$-$C_6$ alkyl, —(C═O)$(CH_2)_l$—$ONO_2$; —(C═O)$(CH_2)_m$—$CH(NH_2)CH_2ONO_2$;

$R_2$ is H or $C_1$-$C_6$ alkyl;

$R_7$ and $R_7'$ are independently H, halogen, or $C_1$-$C_6$ alkyl;

X, Y, and Z are independently absent, O, S, NH and —O—(P═O)OHO—, m is 2, 3, or 4; and each n is independently 1, 2, 3, 4 or 5;

wherein at least one of $R_1$, $R_3$, $R_4$, $R_5$ and $R_6$ is —(C═O)$(CR_7R_7')_n$—$ONO_2$, —(C═O)$(CR_7R_7')_m$—$CH(NH_2)CH_2ONO_2$.

In embodiments, the present disclosure provides a pharmaceutical composition, comprising a compound of the present disclosure (e.g., compounds of Formula (I), (II) or Table 1) and a pharmaceutically acceptable excipient.

In embodiments, the present disclosure provides methods of using one or more compounds of the present disclosure (e.g., compounds of Formula (I), (II) or Table 1), e.g., as NO delivery agents.

DETAILED DESCRIPTION OF THE INVENTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "administer," "administering" or "administration" as used herein refer to administering a compound or pharmaceutically acceptable salt of the compound or a composition or formulation comprising the compound or pharmaceutically acceptable salt of the compound to a patient.

The term "treating" as used herein with regard to a patient or subject, refers to improving at least one symptom of the patient's or subject's disorder. In some embodiments, treating can be improving, or at least partially ameliorating a disorder or one or more symptoms of a disorder.

The term "therapeutically effective" applied to dose or amount refers to that quantity of a compound or pharmaceutical formulation that is sufficient to result in a desired clinical benefit after administration to a patient or subject in need thereof.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

The term "substituted" used herein means any of the groups described herein (e.g., alkyl, alkenyl, alkynyl, alkoxy, aryl, cycloalkyl, cycloalkenyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_7R_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

Compounds

In embodiments, the present disclosure provides dimethyltryptamine derivatives that release nitric oxide (NO) in vivo. In embodiments, the present disclosure provides prodrugs of dimethyltryptamine and derivatives thereof. In embodiments, the present disclosure provides compound of Formula (I) and (II), or pharmaceutically acceptable salts thereof.

In embodiments, the present disclosure provides a compound of Formula (I):

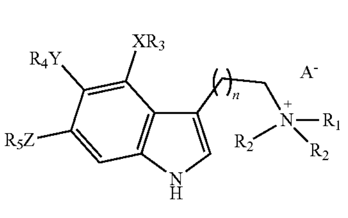

or a pharmaceutically acceptable salt thereof; wherein, $R_1$, $R_3$, $R_4$ and $R_5$ are independently H, halogen, $C_1$-$C_6$ alkyl, $-(C=O)(CR_7R_7')_n-ONO_2$, or $-(C=O)(CR_7R_7')_m-CH(NH_2)CH_2ONO_2$;

$R_2$ is independently $C_1$-$C_6$ alkyl;

X, Y, and Z are independently absent, H, O, S, NH and $-O-(P=O)OHO-$;

m is 2, 3, or 4;

each n is independently 1, 2, 3, 4 or 5; and $A^-$ is a pharmaceutically acceptable anion, wherein at least one of $R_1$, $R_3$, $R_4$ and $R_5$ are —(C═O)$(CR_7R_7')_n$—$ONO_2$ or —(C═O)$(CR_7R_7')_m$—CH($NH_2$)$CH_2ONO_2$.

In embodiments of the compounds of Formula (I), $R_1$ is $C_1$-$C_6$ alkyl. In embodiments of the compounds of Formula (I), $R_1$ is methyl, ethyl, or propyl. In embodiments of the compounds of Formula (I), $R_1$ is methyl. In embodiments of the compounds of Formula (I), $R_1$ is H.

In embodiments of the compounds of Formula (I), $R_1$ is $C_1$-$C_6$ alkyl, —(C═O)$(CR_7R_7')_n$—$ONO_2$, or —(C═O)$(CR_7R_7')_m$—CH($NH_2$)$CH_2ONO_2$. In embodiments of the compounds of Formula (I), $R_1$ is H, —(C═O)$(CR_7R_7')_n$—$ONO_2$, or —(C═O)$(CR_7R_7')_m$—CH($NH_2$)$CH_2ONO_2$. In embodiments of the compounds of Formula (I), $R_1$ is H, $C_1$-$C_6$ alkyl, or —(C═O)$(CR_7R_7')_m$—CH($NH_2$)$CH_2ONO_2$. In embodiments of the compounds of Formula (I), $R_1$ is H, $C_1$-$C_6$ alkyl, or —(C═O)$(CR_7R_7')_n$—$ONO_2$. In embodiments of the compounds of Formula (I), $R_1$ is —(C═O)$(CR_7R_7')_n$—$ONO_2$ or —(C═O)$(CR_7R_7')_m$—CH($NH_2$)$CH_2ONO_2$. In embodiments of the compounds of Formula (I), $R_1$ is $C_1$-$C_6$ alkyl or —(C═O)$(CR_7R_7')_m$—CH($NH_2$)$CH_2ONO_2$. In embodiments of the compounds of Formula (I), $R_1$ is halogen, $C_1$-$C_6$ alkyl, —(C═O)$(CR_7R_7')_n$—$ONO_2$, or —(C═O)$(CR_7R_7')_m$—CH($NH_2$)$CH_2ONO_2$.

In embodiments of the compounds of Formula (I), $R_1$ is —(C═O)$(CR_7R_7')_n$—$ONO_2$. In embodiments of the compounds of Formula (I), $R_1$ is —(C═O)$(CR_7R_7')_m$—CH($NH_2$)$CH_2ONO_2$. In embodiments of the compounds of Formula (I), $R_1$ is —(C═O)$(CH_2)_n$—$ONO_2$. In embodiments of the compounds of Formula (I), $R_1$ is —(C═O)$(CH_2)_m$—CH($NH_2$)$CH_2ONO_2$. In embodiments of the compounds of Formula (I), $R_1$ is —(C═O)$(CH_2)_3$—$ONO_2$. In embodiments of the compounds of Formula (I), $R_1$ is —(C═O)$(CH_2)_2$—CH($NH_2$)$CH_2ONO_2$.

In embodiments of the compounds of Formula (I), $R_3$ is H. In embodiments of the compounds of Formula (I), $R_3$ is halogen. In embodiments of the compounds of Formula (I), $R_3$ is $C_1$-$C_6$ alkyl.

In embodiments of the compounds of Formula (I), $R_3$ is H, $C_1$-$C_6$ alkyl, —(C═O)$(CR_7R_7')_n$—$ONO_2$, —(C═O)$(CR_7R_7')_m$—CH($NH_2$)$CH_2ONO_2$. In embodiments of the compounds of Formula (I), $R_3$ is H, halogen, —(C═O)$(CR_7R_7')_n$—$ONO_2$, —(C═O)$(CR_7R_7')_m$—CH($NH_2$)$CH_2ONO_2$. In embodiments of the compounds of Formula (I), $R_3$ is H, halogen, $C_1$-$C_6$ alkyl, or —(C═O)$(CR_7R_7')_m$—CH($NH_2$)$CH_2ONO_2$. In embodiments of the compounds of Formula (I), $R_3$ is H, halogen, $C_1$-$C_6$ alkyl, or —(C═O)$(CR_7R_7')_n$—$ONO_2$. In embodiments of the compounds of Formula (I), $R_3$ is H, halogen, or $C_1$-$C_6$ alkyl. In embodiments of the compounds of Formula (I), $R_3$ is H or halogen. In embodiments of the compounds of Formula (I), $R_3$ is H or $C_1$-$C_6$ alkyl. In embodiments of the compounds of Formula (I), $R_3$ is halogen or $C_1$-$C_6$ alkyl.

In embodiments of the compounds of Formula (I), $R_3$ is —(C═O)$(CR_7R_7')_n$—$ONO_2$ or —(C═O)$(CR_7R_7')_m$—CH($NH_2$)$CH_2ONO_2$. In embodiments of the compounds of Formula (I), $R_3$ is —(C═O)$(CR_7R_7')_n$—$ONO_2$. In embodiments of the compounds of Formula (I), $R_3$ is —(C═O)$(CR_7R_7')_m$—CH($NH_2$)$CH_2ONO_2$.

In embodiments of the compounds of Formula (I), $R_4$ is H, halogen, or $C_1$-$C_6$ alkyl. In embodiments of the compounds of Formula (I), $R_4$ is H or halogen. In embodiments of the compounds of Formula (I), $R_4$ is H or $C_1$-$C_6$ alkyl. In embodiments of the compounds of Formula (I), $R_4$ is halogen or $C_1$-$C_6$ alkyl.

In embodiments of the compounds of Formula (I), $R_4$ is halogen, $C_1$-$C_6$ alkyl, —(C═O)$(CR_7R_7')_n$—$ONO_2$, —(C═O)$(CR_7R_7')_m$—CH($NH_2$)$CH_2ONO_2$. In embodiments of the compounds of Formula (I), $R_4$ is H, $C_1$-$C_6$ alkyl, —(C═O)$(CR_7R_7')_n$—$ONO_2$, —(C═O)$(CR_7R_7')_m$—CH($NH_2$)$CH_2ONO_2$. In embodiments of the compounds of Formula (I), $R_4$ is H, halogen, —(C═O)$(CR_7R_7')_n$—$ONO_2$, —(C═O)$(CR_7R_7')_m$—CH($NH_2$)$CH_2ONO_2$. In embodiments of the compounds of Formula (I), $R_4$ is H, halogen, $C_1$-$C_6$ alkyl, or —(C═O)$(CR_7R_7')_m$—CH($NH_2$)$CH_2ONO_2$. In embodiments of the compounds of Formula (I), $R_4$ is H, halogen, $C_1$-$C_6$ alkyl, or —(C═O)$(CR_7R_7')_n$—$ONO_2$.

In embodiments of the compounds of Formula (I), $R_4$ is —(C═O)$(CR_7R_7')_n$—$ONO_2$ or —(C═O)$(CR_7R_7')_m$—CH($NH_2$)$CH_2ONO_2$. In embodiments of the compounds of Formula (I), $R_4$ is —(C═O)$(CR_7R_7')_n$—$ONO_2$. In embodiments of the compounds of Formula (I), $R_4$ is —(C═O)$(CR_7R_7')_m$—CH($NH_2$)$CH_2ONO_2$.

In embodiments of the compounds of Formula (I), $R_5$ is H. In embodiments of the compounds of Formula (I), $R_5$ is halogen. In embodiments of the compounds of Formula (I), $R_5$ is $C_1$-$C_6$ alkyl. In embodiments of the compounds of Formula (I), $R_5$ is H, halogen, or $C_1$-$C_6$ alkyl. In embodiments of the compounds of Formula (I), $R_5$ is H or halogen. In embodiments of the compounds of Formula (I), $R_5$ is H or $C_1$-$C_6$ alkyl. In embodiments of the compounds of Formula (I), $R_5$ is halogen or $C_1$-$C_6$ alkyl.

In embodiments of the compounds of Formula (I), $R_5$ is halogen, $C_1$-$C_6$ alkyl, —(C═O)$(CR_7R_7')_n$—$ONO_2$, —(C═O)$(CR_7R_7')_m$—CH($NH_2$)$CH_2ONO_2$. In embodiments of the compounds of Formula (I), $R_5$ is H, $C_1$-$C_6$ alkyl, —(C═O)$(CR_7R_7')_n$—$ONO_2$, —(C═O)$(CR_7R_7')_m$—CH($NH_2$)$CH_2ONO_2$. In embodiments of the compounds of Formula (I), $R_5$ is H, halogen, —(C═O)$(CR_7R_7')_n$—$ONO_2$, —(C═O)$(CR_7R_7')_m$—CH($NH_2$)$CH_2ONO_2$. In embodiments of the compounds of Formula (I), $R_5$ is H, halogen, $C_1$-$C_6$ alkyl, or —(C═O)$(CR_7R_7')_m$—CH($NH_2$)$CH_2ONO_2$. In embodiments of the compounds of Formula (I), $R_5$ is H, halogen, $C_1$-$C_6$ alkyl, or —(C═O)$(CR_7R_7')_n$—$ONO_2$.

In embodiments of the compounds of Formula (I), $R_5$ is —(C═O)$(CR_7R_7')_n$—$ONO_2$ or —(C═O)$(CR_7R_7')_m$—CH($NH_2$)$CH_2ONO_2$. In embodiments of the compounds of Formula (I), $R_5$ is —(C═O)$(CR_7R_7')_n$—$ONO_2$. In embodiments of the compounds of Formula (I), $R_5$ is —(C═O)$(CR_7R_7')_m$—CH($NH_2$)$CH_2ONO_2$.

In embodiments of the compounds of Formula (I), $R_7$ and $R_7'$ are independently H or $C_1$-$C_6$alkyl. In embodiments of the compounds of Formula (I), $R_7$ and $R_7'$ are independently H or $C_1$-$C_3$alkyl. In embodiments of the compounds of Formula (I), $R_7$ and $R_7'$ are independently H or halogen alkyl. In embodiments of the compounds of Formula (I), $R_7$ and $R_7'$ are independently halogen or $C_1$-$C_6$ alkyl. In embodiments of the compounds of Formula (I), $R_7$ and $R_7'$ are independently halogen or $C_1$-$C_3$ alkyl.

In embodiments of the compounds of Formula (I), X is O, S, NH and —O—(P═O)OHO—. In embodiments of the compounds of Formula (I), X is absent, S, NH and —O—(P═O)OHO—. In embodiments of the compounds of Formula (I), X is absent, O, S or —O—(P═O)OHO—. In embodiments of the compounds of Formula (I), X is absent, O, S, or NH. In embodiments of the compounds of Formula (I), X is O or —O—(P═O)OHO—.

In embodiments of the compounds of Formula (I), X is absent. In embodiments of the compounds of Formula (I), X is O. In embodiments of the compounds of Formula (I), X is S. In embodiments of the compounds of Formula (I), X is NH. In embodiments of the compounds of Formula (I), X is —O—(P═O)OHO—.

In embodiments of the compounds of Formula (I), Y is O, S, NH and —O—(P═O)OHO—. In embodiments of the compounds of Formula (I), Y is absent, S, NH and —O—(P═O)OHO—. In embodiments of the compounds of Formula (I), Y is absent, O, S or —O—(P═O)OHO—. In embodiments of the compounds of Formula (I), Y is absent, O, S, or NH. In embodiments of the compounds of Formula (I), Y is O or —O—(P═O)OHO—.

In embodiments of the compounds of Formula (I), Y is absent. In embodiments of the compounds of Formula (I), Y is O. In embodiments of the compounds of Formula (I), Y is S. In embodiments of the compounds of Formula (I), Y is NH. In embodiments of the compounds of Formula (I), Y is —O—(P═O)OHO—.

In embodiments of the compounds of Formula (I), Z is O, S, NH and —O—(P═O)OHO—. In embodiments of the compounds of Formula (I), Z is absent, S, NH and —O—(P═O)OHO—. In embodiments of the compounds of Formula (I), Z is absent, O, S or —O—(P═O)OHO—. In embodiments of the compounds of Formula (I), Z is absent, O, S, or NH. In embodiments of the compounds of Formula (I), Z is O or —O—(P═O)OHO—.

In embodiments of the compounds of Formula (I), Z is absent. In embodiments of the compounds of Formula (I), Z is O. In embodiments of the compounds of Formula (I), Z is S. In embodiments of the compounds of Formula (I), Z is NH. In embodiments of the compounds of Formula (I), Z is —O—(P═O)OHO—.

In embodiments of the compounds of Formula (I), n is 1. In embodiments of the compounds of Formula (I), n is 2. In embodiments of the compounds of Formula (I), n is 3. In embodiments of the compounds of Formula (I), n is 4. In embodiments of the compounds of Formula (I), n is 5.

In embodiments of the compounds of Formula (I), m is 2. In embodiments of the compounds of Formula (I), m is 3. In embodiments of the compounds of Formula (I), m is 4. In embodiments of the compounds of Formula (I), m is 5.

In embodiments of the compounds of Formula (I), $R_3$ is H and X is absent. In embodiments of compounds of Formula (I), $R_3$ is halogen and X is absent. In embodiments of compounds of Formula (I), $R_3$ is H and X is O. In embodiments of compounds of Formula (I), $R_3$ is $C_1$-$C_6$ alkyl and X is O. In embodiments of compounds of Formula (I), $R_3$ is Cl, F, Br, or I and X is absent. In embodiments of compounds of Formula (I), $R_3$ is F and X is absent.

In embodiments of the compounds of Formula (I), $R_4$ is H and Y is absent. In embodiments of compounds of Formula (I), $R_4$ is halogen and Y is absent. In embodiments of compounds of Formula (I), $R_4$ is H and Y is O. In embodiments of compounds of Formula (II), $R_4$ is $C_1$-$C_6$ alkyl and Y is O. In embodiments of compounds of Formula (I), $R_4$ is Cl, F, Br, or I and Y is absent. In embodiments of compounds of Formula (I), $R_4$ is F and Y is absent In embodiments of the compounds of Formula (I), $R_5$ is H and Z is absent. In embodiments of compounds of Formula (I), $R_5$ is halogen and Z is absent. In embodiments of compounds of Formula (I), $R_5$ is H and Z is O. In embodiments of compounds of Formula (I), $R_5$ is $C_1$-$C_6$ alkyl and Z is O. In embodiments of compounds of Formula (I), $R_5$ is Cl, F, Br, or I and Z is absent. In embodiments of compounds of Formula (II), $R_5$ is F and Z is absent.

Formula (II):

In embodiments, provided herein is a compound of Formula (II):

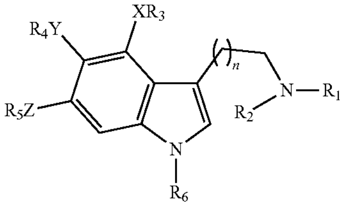

or a pharmaceutically acceptable salt thereof; wherein, $R_3$, $R_4$, and $R_5$ are independently H, halogen, $C_1$-$C_6$ alkyl, —(C═O)$(CR_7R_7')_n$—$ONO_2$, or —(C═O)$(CR_7R_7')_m$—CH($NH_2$)$CH_2ONO_2$;

$R_1$ and $R_6$ are independently H, $C_1$-$C_6$ alkyl, —(C═O)$(CR_7R_7')_n$—$ONO_2$, or —(C═O)$(CR_7R_7')_m$—CH($NH_2$)$CH_2ONO_2$;

$R_2$ is H or $C_1$-$C_6$ alkyl; and $R_7$ and $R_7'$ are independently H, halogen, or $C_1$-$C_6$ alkyl;

X, Y, and Z are independently absent, O, S, NH and —O—(P═O)OHO—, m is 2, 3, or 4; and each n is independently 1, 2, 3, 4 or 5;

wherein at least one of $R_1$, $R_3$, $R_4$, $R_5$ and $R_6$ is —(C═O)$(CR_7R_7')_n$—$ONO_2$, —(C═O)$(CR_7R_7')_m$—CH($NH_2$)$CH_2ONO_2$.

In embodiments of the compounds of Formula (II), $R_1$ is $C_1$-$C_6$ alkyl. In embodiments of the compounds of Formula (II), $R_1$ is methyl, ethyl, or propyl. In embodiments of the compounds of Formula (II), $R_1$ is methyl. In embodiments of the compounds of Formula (II), $R_1$ is H.

In embodiments of the compounds of Formula (II), $R_1$ is —(C═O)$(CR_7R_7')_n$—$ONO_2$.

In embodiments of the compounds of Formula (II), $R_1$ is —(C═O)$(CR_7R_7')_m$—CH($NH_2$)$CH_2ONO_2$. In embodiments of the compounds of Formula (II), $R_1$ is —(C═O)$(CH_2)_n$—$ONO_2$. In embodiments of the compounds of Formula (II), $R_1$ is —(C═O)$(CH_2)_m$—CH($NH_2$)$CH_2ONO_2$. In embodiments of the compounds of Formula (II), $R_1$ is —(C═O)$(CH_2)_3$—$ONO_2$. In embodiments of the compounds of Formula (II), $R_1$ is —(C═O)$(CH_2)_2$—CH($NH_2$)$CH_2ONO_2$.

In embodiments of the compounds of Formula (II), $R_1$ is $C_1$-$C_6$ alkyl, —(C═O)$(CR_7R_7')_n$—$ONO_2$, or —(C═O)$(CR_7R_7')_m$—CH($NH_2$)$CH_2ONO_2$. In embodiments of the compounds of Formula (II), $R_1$ is H, —(C═O)$(CR_7R_7')_n$—$ONO_2$, or —(C═O)$(CR_7R_7')_m$—CH($NH_2$)$CH_2ONO_2$. In embodiments of the compounds of Formula (II), $R_1$ is H, $C_1$-$C_6$ alkyl, or —(C═O)$(CR_7R_7')_m$—CH($NH_2$)$CH_2ONO_2$. In embodiments of the compounds of Formula (II), $R_1$ is H, $C_1$-$C_6$ alkyl, or —(C═O)$(CR_7R_7')_n$—$ONO_2$. In embodiments of the compounds of Formula (II), $R_1$ is —(C═O)$(CR_7R_7')_n$—$ONO_2$ or —(C═O)$(CR_7R_7')_m$—CH($NH_2$)$CH_2ONO_2$. In embodiments of the compounds of Formula (II), $R_1$ is $C_1$-$C_6$ alkyl or —(C═O)$(CR_7R_7')_m$—CH($NH_2$)$CH_2ONO_2$. In embodiments of the compounds of Formula (II), $R_1$ is $C_1$-$C_6$ alkyl, or —(C═O)(is halogen, $C_1$-$C_6$ alkyl, —(C═O)$(CR_7R_7')_n$—$ONO_2$, —(C═O)$(CR_7R_7')_m$—CH($NH_2$)$CH_2ONO_2$.

In embodiments of the compounds of Formula (II), $R_3$ is H, halogen, or $C_1$-$C_6$ alkyl. In embodiments of the compounds of Formula (II), $R_3$ is H or halogen. In embodiments of the compounds of Formula (II), $R_3$ is H or $C_1$-$C_6$ alkyl. In embodiments of the compounds of Formula (II), $R_3$ is halogen or $C_1$-$C_6$ alkyl. In embodiments of the compounds of Formula (II), $R_3$ is H. In embodiments of the compounds of Formula (II), $R_3$ is halogen. In embodiments of the compounds of Formula (II), $R_3$ is $C_1$-$C_6$ alkyl.

In embodiments of the compounds of Formula (II), $R_3$ is H, $C_1$-$C_6$ alkyl, —(C═O)($CR_7R_7'$)$_n$—$ONO_2$, —(C═O)($CR_7R_7'$)$_m$—CH($NH_2$)$CH_2ONO_2$. In embodiments of the compounds of Formula (II), $R_3$ is H, halogen, —(C═O)($CR_7R_7'$)$_n$—$ONO_2$, —(C═O)($CR_7R_7'$)$_m$—CH($NH_2$)$CH_2ONO_2$.

In embodiments of the compounds of Formula (II), $R_3$ is H, halogen, $C_1$-$C_6$ alkyl, or —(C═O)($CR_7R_7'$)$_m$—CH($NH_2$)$CH_2ONO_2$. In embodiments of the compounds of Formula (II), $R_3$ is H, halogen, $C_1$-$C_6$ alkyl, or —(C═O)($CR_7R_7'$)$_n$—$ONO_2$. In embodiments of the compounds of Formula (II), $R_3$ is —(C═O)($CR_7R_7'$)$_n$—$ONO_2$ or —(C═O)($CR_7R_7'$)$_m$—CH($NH_2$)$CH_2ONO_2$. In embodiments of the compounds of Formula (II), $R_3$ is —(C═O)($CR_7R_7'$)$_n$—$ONO_2$. In embodiments of the compounds of Formula (II), $R_3$ is —(C═O)($CR_7R_7'$)$_m$—CH($NH_2$)$CH_2ONO_2$.

In embodiments of the compounds of Formula (II), $R_4$ is H, halogen, or $C_1$-$C_6$ alkyl. In embodiments of the compounds of Formula (II), $R_4$ is H or halogen. In embodiments of the compounds of Formula (II), $R_4$ is H or $C_1$-$C_6$ alkyl. In embodiments of the compounds of Formula (II), $R_4$ is halogen or $C_1$-$C_6$ alkyl.

In embodiments of the compounds of Formula (II), $R_4$ is halogen, $C_1$-$C_6$ alkyl, —(C═O)($CR_7R_7'$)$_n$—$ONO_2$, —(C═O)($CR_7R_7'$)$_m$—CH($NH_2$)$CH_2ONO_2$. In embodiments of the compounds of Formula (II), $R_4$ is H, $C_1$-$C_6$ alkyl, —(C═O)($CR_7R_7'$)$_n$—$ONO_2$, —(C═O)($CR_7R_7'$)$_m$—CH($NH_2$)$CH_2ONO_2$. In embodiments of the compounds of Formula (II), $R_4$ is H, halogen, —(C═O)($CR_7R_7'$)$_n$—$ONO_2$, —(C═O)($CR_7R_7'$)$_m$—CH($NH_2$)$CH_2ONO_2$. In embodiments of the compounds of Formula (II), $R_4$ is H, halogen, $C_1$-$C_6$ alkyl, or —(C═O)($CR_7R_7'$)$_m$—CH($NH_2$)$CH_2ONO_2$. In embodiments of the compounds of Formula (II), $R_4$ is H, halogen, $C_1$-$C_6$ alkyl, or —(C═O)($CR_7R_7'$)$_n$—$ONO_2$. In embodiments of the compounds of Formula (II), $R_4$ is —(C═O)($CR_7R_7'$)$_n$—$ONO_2$ or —(C═O)($CR_7R_7'$)$_m$—CH($NH_2$)$CH_2ONO_2$. In embodiments of the compounds of Formula (II), $R_4$ is —(C═O)($CR_7R_7'$)$_n$—$ONO_2$. In embodiments of the compounds of Formula (II), $R_4$ is —(C═O)($CR_7R_7'$)$_m$—CH($NH_2$)$CH_2ONO_2$.

In embodiments of the compounds of Formula (II), $R_5$ is H, halogen, or $C_1$-$C_6$ alkyl. In embodiments of the compounds of Formula (II), $R_5$ is H or halogen. In embodiments of the compounds of Formula (II), $R_5$ is H or $C_1$-$C_6$ alkyl. In embodiments of the compounds of Formula (II), $R_5$ is halogen or $C_1$-$C_6$ alkyl. In embodiments of the compounds of Formula (II), $R_5$ is H. In embodiments of the compounds of Formula (II), $R_5$ is halogen. In embodiments of the compounds of Formula (II), $R_5$ is $C_1$-$C_6$ alkyl.

In embodiments of the compounds of Formula (II), $R_5$ is halogen, $C_1$-$C_6$ alkyl, —(C═O)($CR_7R_7'$)$_n$—$ONO_2$, —(C═O)($CR_7R_7'$)$_m$—CH($NH_2$)$CH_2ONO_2$. In embodiments of the compounds of Formula (II), $R_5$ is H, $C_1$-$C_6$ alkyl, —(C═O)($CR_7R_7'$)$_n$—$ONO_2$, —(C═O)($CR_7R_7'$)$_m$—CH($NH_2$)$CH_2ONO_2$. In embodiments of the compounds of Formula (II), $R_5$ is H, halogen, —(C═O)($CR_7R_7'$)$_n$—$ONO_2$, —(C═O)($CR_7R_7'$)$_m$—CH($NH_2$)$CH_2ONO_2$. In embodiments of the compounds of Formula (II), $R_5$ is H, halogen, $C_1$-$C_6$ alkyl, or —(C═O)($CR_7R_7'$)$_m$—CH($NH_2$)$CH_2ONO_2$. In embodiments of the compounds of Formula (II), $R_5$ is H, halogen, $C_1$-$C_6$ alkyl, or —(C═O)($CR_7R_7'$)$_n$—$ONO_2$. In embodiments of the compounds of Formula (II), $R_5$ is —(C═O)($CR_7R_7'$)$_n$—$ONO_2$ or —(C═O)($CR_7R_7'$)$_m$—CH($NH_2$)$CH_2ONO_2$. In embodiments of the compounds of Formula (II), $R_5$ is —(C═O)($CR_7R_7'$)$_n$—$ONO_2$. In embodiments of the compounds of Formula (II), $R_5$ is —(C═O)($CR_7R_7'$)$_m$—CH($NH_2$)$CH_2ONO_2$.

In embodiments of the compounds of Formula (II), $R_6$ is H or $C_1$-$C_6$ alkyl. In embodiments of the compounds of Formula (II), $R_6$ is $C_1$-$C_6$ alkyl. In embodiments of the compounds of Formula (II), $R_6$ is methyl, ethyl, or propyl. In embodiments of the compounds of Formula (II), $R_6$ is methyl.

In embodiments of the compounds of Formula (II), $R_6$ is H.

In embodiments of the compounds of Formula (II), $R_6$ is —(C═O)($CR_7R_7'$)$_n$—$ONO_2$.

In embodiments of the compounds of Formula (II), $R_6$ is —(C═O)($CR_7R_7'$)$_m$—CH($NH_2$)$CH_2ONO_2$. In embodiments of the compounds of Formula (II), $R_6$ is —(C═O)($CH_2$)$_n$—$ONO_2$. In embodiments of the compounds of Formula (II), $R_6$ is —(C═O)($CH_2$)$_m$—CH($NH_2$)$CH_2ONO_2$. In embodiments of the compounds of Formula (II), $R_6$ is —(C═O)($CH_2$)$_3$—$ONO_2$. In embodiments of the compounds of Formula (II), $R_6$ is —(C═O)($CH_2$)$_2$—CH($NH_2$)$CH_2ONO_2$. In embodiments of the compounds of Formula (II), $R_6$ is $C_1$-$C_6$ alkyl, —(C═O)($CR_7R_7'$)$_n$—$ONO_2$, or —(C═O)($CR_7R_7'$)$_m$—CH($NH_2$)$CH_2ONO_2$. In embodiments of the compounds of Formula (II), $R_6$ is H, —(C═O)($CR_7R_7'$)$_n$—$ONO_2$, or —(C═O)($CR_7R_7'$)$_m$—CH($NH_2$)$CH_2ONO_2$. In embodiments of the compounds of Formula (II), $R_6$ is H, $C_1$-$C_6$ alkyl, or —(C═O)($CR_7R_7'$)$_m$—CH($NH_2$)$CH_2ONO_2$. In embodiments of the compounds of Formula (II), $R_6$ is H, $C_1$-$C_6$ alkyl, or —(C═O)($CR_7R_7'$)$_n$—$ONO_2$. In embodiments of the compounds of Formula (II), $R_6$ is —(C═O)($CR_7R_7'$)$_n$—$ONO_2$ or —(C═O)($CR_7R_7'$)$_m$—CH($NH_2$)$CH_2ONO_2$. In embodiments of the compounds of Formula (II), $R_6$ is $C_1$-$C_6$ alkyl or —(C═O)($CR_7R_7'$)$_m$—CH($NH_2$)$CH_2ONO_2$.

In embodiments of the compounds of Formula (II), $R_6$ is $C_1$-$C_6$ alkyl, or —(C═O)($CR_7R_7'$)$_n$—$ONO_2$. In embodiments of the compounds of Formula (II), $R_6$ is H or —(C═O)($CR_7R_7'$)$_n$—$ONO_2$. In embodiments of the compounds of Formula (II), $R_6$ is H or —(C═O)($CR_7R_7'$)$_m$—CH($NH_2$)$CH_2ONO_2$.

In embodiments of the compounds of Formula (II), $R_7$ and $R_7'$ are independently H or $C_1$-$C_6$alkyl. In embodiments of the compounds of Formula (II), $R_7$ and $R_7'$ are independently H or $C_1$-$C_3$ alkyl. In embodiments of the compounds of Formula (II), $R_7$ and $R_7'$ are independently H or halogen alkyl. In embodiments of the compounds of Formula (II), $R_7$ and $R_7'$ are independently halogen or $C_1$-$C_6$ alkyl. In embodiments of the compounds of Formula (II), $R_7$ and $R_7'$ are independently halogen or $C_1$-$C_3$ alkyl.

In embodiments of the compounds of Formula (II), X is O, S, NH and —O—(P═O)OHO—. In embodiments of the compounds of Formula (II), X is absent, S, NH and —O—(P═O)OHO—. In embodiments of the compounds of Formula (II), X is absent, O, S or —O—(P═O)OHO—. In embodiments of the compounds of Formula (II), X is absent, O, S, or NH. In embodiments of the compounds of Formula (II), X is absent. In embodiments of the compounds of Formula (II), X is O. In embodiments of the compounds of Formula (II), X is S. In embodiments of the compounds of Formula (II), X is NH. In embodiments of the compounds of Formula (II), X is —O—(P═O)OHO—. In embodiments of the compounds of Formula (II), X is O or —O—(P═O)OHO—.

In embodiments of the compounds of Formula (II), Y is O, S, NH and —O—(P═O)OHO—. In embodiments of the compounds of Formula (II), Y is absent, S, NH and —O—(P═O)OHO—. In embodiments of the compounds of Formula (II), Y is absent, O, S or —O—(P═O)OHO—. In embodiments of the compounds of Formula (II), Y is absent, O, S, or NH. In embodiments of the compounds of Formula (II), Y is absent. In embodiments of the compounds of Formula (II), Y is O. In embodiments of the compounds of Formula (II), Y is S. In embodiments of the compounds of Formula (II), Y is NH. In embodiments of the compounds of Formula (II), Y is —O—(P═O)OHO—. In embodiments of the compounds of Formula (II), Y is O or —O—(P═O)OHO—.

In embodiments of the compounds of Formula (II), Z is O, S, NH and —O—(P═O)OHO—. In embodiments of the compounds of Formula (II), Z is absent, S, NH and —O—(P═O)OHO—. In embodiments of the compounds of Formula (II), Z is absent, O, S or —O—(P═O)OHO—. In embodiments of the compounds of Formula (II), Z is absent, O, S, or NH. In embodiments of the compounds of Formula (II), Z is absent. In embodiments of the compounds of Formula (II), Z is O. In embodiments of the compounds of Formula (II), Z is S. In embodiments of the compounds of Formula (II), Z is NH. In embodiments of the compounds of Formula (II), Z is —O—(P═O)OHO—. In embodiments of the compounds of Formula (II), Z is O or —O—(P═O)OHO—.

In embodiments of the compounds of Formula (II), n is 1. In embodiments of the compounds of Formula (II), n is 2. In embodiments of the compounds of Formula (II), n is 3. In embodiments of the compounds of Formula (II), n is 4. In embodiments of the compounds of Formula (II), n is 5.

In embodiments of the compounds of Formula (II), m is 2. In embodiments of the compounds of Formula (II), m is 3. In embodiments of the compounds of Formula (II), m is 4. In embodiments of the compounds of Formula (II), m is 5.

In embodiments of the compounds of Formula (II), $R_3$ is H and X is absent. In embodiments of compounds of Formula (II), $R_3$ is halogen and X is absent. In embodiments of compounds of Formula (II), $R_3$ is H and X is O. In embodiments of compounds of Formula (II), $R_3$ is $C_1$-$C_6$ alkyl and X is O. In embodiments of compounds of Formula (II), $R_3$ is Cl, F, Br, or I and X is absent. In embodiments of compounds of Formula (II), $R_3$ is F and X is absent.

In embodiments of the compounds of Formula (II), $R_4$ is H and Y is absent. In embodiments of compounds of Formula (II), $R_4$ is halogen and Y is absent. In embodiments of compounds of Formula (II), $R_4$ is H and Y is O. In embodiments of compounds of Formula (II), $R_4$ is $C_1$-$C_6$ alkyl and Y is O. In embodiments of compounds of Formula (II), $R_4$ is Cl, F, Br, or I and Y is absent. In embodiments of compounds of (Formula (II), $R_4$ is F and Y is absent.

In embodiments of the compounds of Formula (II), $R_5$ is H and Z is absent. In embodiments of compounds of Formula (II), $R_5$ is halogen and Z is absent. In embodiments of compounds of Formula (II), $R_5$ is H and Z is O. In embodiments of compounds of Formula (II), $R_5$ is $C_1$-$C_6$ alkyl and Z is O. In embodiments of compounds of Formula (II), $R_5$ is Cl, F, Br, or I and Z is absent. In embodiments of compounds of Formula (II), $R_5$ is F and Z is absent.

TABLE 1

Compounds of Formula (II)

| No. | Structure | |
|---|---|---|
| 2-1 | 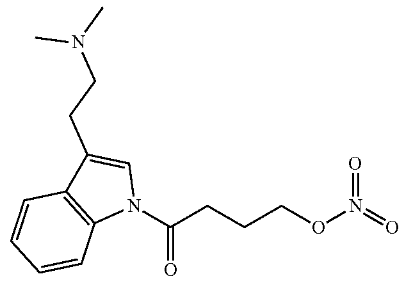 [SMILES: CN(C)CCc1cn(C(=O)CCCO[N+](=O)[O-])c2ccccc12] | 4-(3-(2-(dimethylamino)ethyl)-1H-indol-1-yl)-4-oxobutyl nitrate |
| 2-2 | 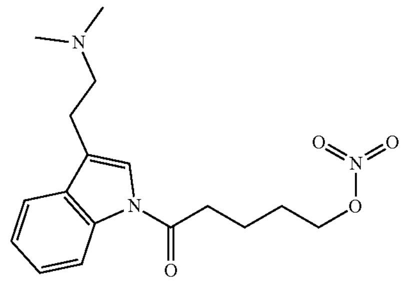 [SMILES: CN(C)CCc1cn(C(=O)CCCCO[N+](=O)[O-])c2ccccc12] | 5-(3-(2-(dimethylamino)ethyl)-1H-indol-1-yl)-5-oxopentyl nitrate |

TABLE 1-continued
| No. | Structure | |
|---|---|---|
| | Compounds of Formula (II) | |
| 2-3 | 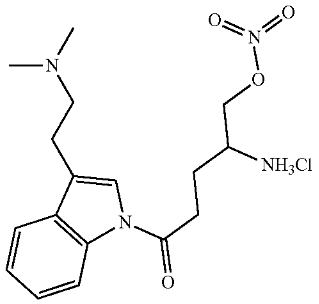 | 2-(chloro-λ5-azaneyl)-5-(3-(2-(dimethylamino)ethyl)-1H-indol-1-yl)-5-oxopentyl nitrate |
| 2-4 | 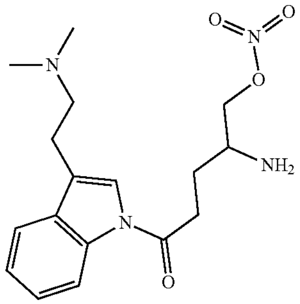 [SMILES: CN(C)CCc1cn(C(=O)CCC(N)CO[N+](=O)[O-])c2ccccc12] | 2-amino-5-(3-(2-(dimethylamino)ethyl)-1H-indol-1-yl)-5-oxopentyl nitrate |
| 2-5 | 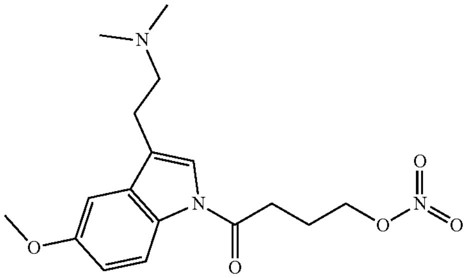 [SMILES: COc1ccc2c(c1)c(CCN(C)C)cn2C(=O)CCCO[N+](=O)[O-]] | 4-(3-(2-(dimethylamino)ethyl)-5-methoxy-1H-indol-1-yl)-4-oxobutyl nitrate |
| 2-6 | 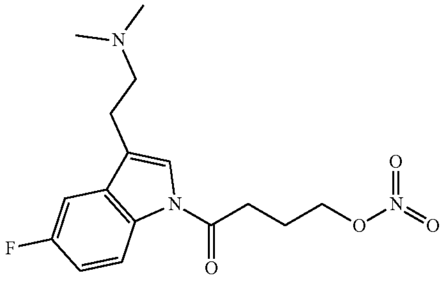 [SMILES: CN(C)CCc1cn(C(=O)CCCO[N+](=O)[O-])c2ccc(F)cc12] | 4-(3-(2-(dimethylamino)ethyl)-5-fluoro-1H-indol-1-yl)-4-oxobutyl nitrate |
| 2-7 | 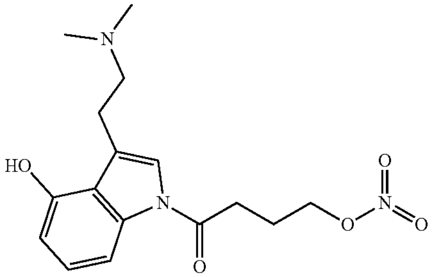 [SMILES: CN(C)CCc1cn(C(=O)CCCO[N+](=O)[O-])c2cccc(O)c12] | 4-(3-(2-(dimethylamino)ethyl)-4-hydroxy-1H-indol-1-yl)-4-oxobutyl nitrate |

TABLE 1-continued
| Compounds of Formula (II) | | |
|---|---|---|
| No. | Structure | |
| 2-8 | 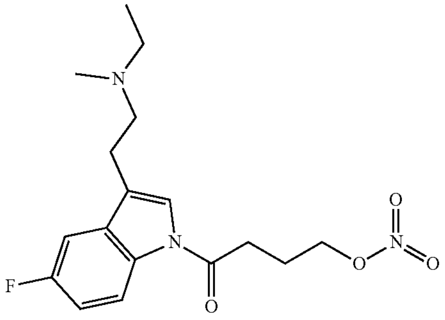 [SMILES: CCN(C)CCc1cn(C(=O)CCCO[N+](=O)[O-])c2ccc(F)cc12] | 4-(3-(2-(ethyl(methyl)amino)ethyl)-5-fluoro-1H-indol-1-yl)-4-oxobutyl nitrate |
| 2-9 | 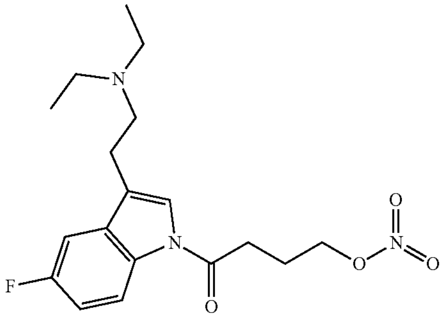 [SMILES: CCN(CC)CCc1cn(C(=O)CCCO[N+](=O)[O-])c2ccc(F)cc12] | 4-(3-(2-(diethylamino)ethyl)-5-fluoro-1H-indol-1-yl)-4-oxobutyl nitrate |
| 2-10 | 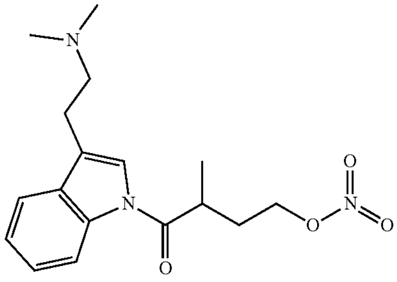 [SMILES: CC(CCO[N+](=O)[O-])C(=O)n1cc(CCN(C)C)c2ccccc21] | 4-(3-(2-(dimethylamino)ethyl)-1H-indol-l-yl)-3-methyl-4-oxobutyl nitrate |
| 2-11 | 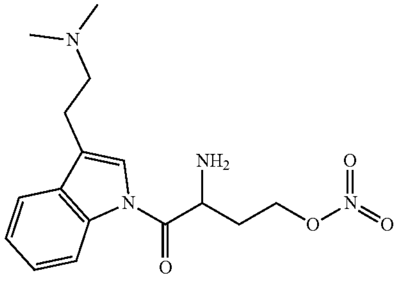 [SMILES: CN(C)CCc1cn(C(=O)C(N)CCO[N+](=O)[O-])c2ccccc12] | 3-amino-4-(3-(2-(dimethylamino)ethyl)-1H-indol-1-yl)-4-oxobutyl nitrate |
| 2-12 | 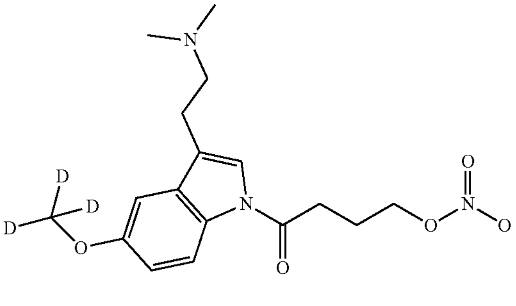 | 4-(3-(2-(dimethylamino)ethyl)-5-(methoxy-$d_3$)-H-indol-1-yl)-4-oxobutyl nitrate |

TABLE 1-continued

| Compounds of Formula (II) | | |
|---|---|---|
| No. | Structure | |
| 2-13 | 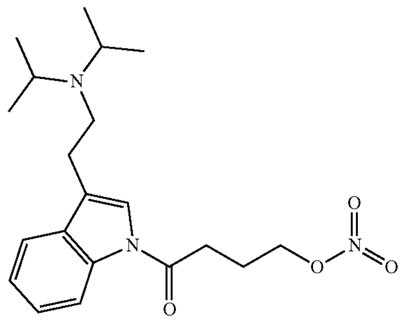 [SMILES: CC(C)N(CCc1cn(C(=O)CCCO[N+](=O)[O-])c2ccccc12)C(C)C] | 4-(3-(2-(diisopropylamino)ethyl)-1H-indol-1-yl)-4-oxobutyl nitrate |
| 2-14 | 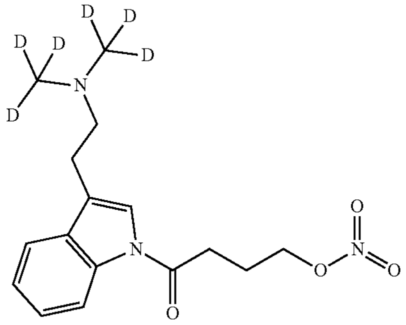 [SMILES: [2H]C([2H])([2H])N(CCc1cn(C(=O)CCCO[N+](=O)[O-])c2ccccc12)C([2H])([2H])[2H]] | 4-(3-(2-(bis(methyl-d3)amino)ethyl)-1H-indol-1-yl)-4-oxobutyl nitrate |

Compositions

In embodiments, the present disclosure provides a pharmaceutical composition comprising a therapeutically effective amount of one or more compounds of the present disclosure (e.g., a compound of Formula (I), (II), or Table 1) or a pharmaceutically acceptable salt thereof and a pharmaceutically acceptable excipient.

The pharmaceutically acceptable excipients and adjuvants are added to the composition or formulation for a variety of purposes. In some embodiments, a pharmaceutical composition comprising one or more compounds disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

Methods of Treatment

In one aspect, the present disclosure provides methods of treating a disease or disorder in a subject in need thereof, the methods comprising administering a therapeutically effective amount of a compound described herein (e.g., a compound of Formula (I), (II), or Table 1) or pharmaceutically acceptable salt thereof to the subject.

In embodiments, the disease or disorder is a mental health disease or disorder. In embodiments, the mental health disease or disorder is selected from the group consisting of major depressive disorder, treatment resistant depression, substance use disorders and eating disorders. In embodiments, eating disorders include illnesses such as anorexia nervosa, bulimia nervosa, and other disorders related to eating (e.g., binge eating).

In embodiments, the mental health disease or disorder is an eating disorder.

In embodiments, the mental health disease or disorder is selected from the group consisting of compulsive disorders, anxiety disorders, stress disorders, and rumination.

In embodiments, the mental health disease or disorder is a mood disorder. In embodiments, mood disorders include e.g., depressive disorders, such as major depressive disorder or treatment resistant depression.

In embodiments, the mental health disorder is a substance abuse disorder. In embodiments, substance use related disorders are disorders of maladaptive patterns of substance use, and include criteria, such as recurrent substance use related problems, tolerance to a substance, withdrawal upon discontinuing use, an inability to cut down or control use of the substance, and giving up important social, occupational, or recreational activities because of using the substance. See e.g., the Diagnostic and Statistical Manual of Mental Disorders (DSM-5). In embodiments, the substance use related disorder is a disorder resulting from the use of: alcohol; caffeine; *cannabis*; hallucinogens (such as phencyclidine or similarly acting arylcyclohexylamines, and other hallucinogens, such as LSD); inhalants; opioids; sedatives, hypnotics, or anxiolytics; stimulants (including amphetamine-type substances, cocaine, and other stimulants); tobacco; and other substances.

In embodiments, administering compounds of the present disclosure (e.g., a compound of Formula (I), (II), or Table 1) or a pharmaceutically acceptable salt thereof releases nitric oxide (NO) (e.g., the compounds of the present disclosure are NO delivery drugs). In embodiments the compounds of the present disclosure are useful for releasing NO in vivo.

NUMBERED EMBODIMENTS

In addition to the disclosure above, the Examples below, and the appended claims, the disclosure sets for the following numbered embodiments.

1. A compound of Formula (II):

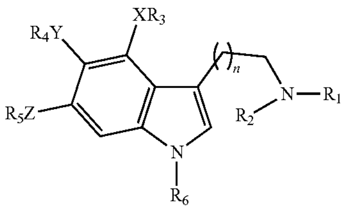

or a pharmaceutically acceptable salt thereof; wherein,
$R_3$, $R_4$, and $R_5$ are independently H, halogen, $C_1$-$C_6$ alkyl, $-(C{=}O)(CR_7R_7')_n-ONO_2$, or $-(C{=}O)(CR_7R_7')_m-CH(NH_2)CH_2ONO_2$;
$R_1$ and $R_6$ are independently H, $C_1$-$C_6$ alkyl, $-(C{=}O)(CR_7R_7')_n-ONO_2$, $-(C{=}O)(CR_7R_7')_m-CH(NH_2)CH_2ONO_2$;
$R_2$ is H or $C_1$-$C_6$ alkyl; and
$R_7$ and $R_7'$ are independently H, halogen, or $C_1$-$C_6$ alkyl;
X, Y, and Z are independently absent, O, S, NH, or $-O-(P{=}O)OHO-$,
m is 2, 3, or 4; and
each n is independently 1, 2, 3, 4 or 5;
wherein at least one of $R_1$, $R_3$, $R_4$, $R_5$ and $R_6$ is $-(C{=}O)(CR_7R_7')_n-ONO_2$, $-(C{=}O)(CR_7R_7')_m-CH(NH_2)CH_2ONO_2$.

2. The compound of embodiment 1, wherein $R_1$ is $C_1$-$C_6$ alkyl.
3. The compound of embodiment 1, wherein $R_1$ is methyl.
4. The compound of embodiment 1, wherein $R_1$ is H.
5. The compound of any one of embodiments 1-4, wherein $R_2$ is $C_1$-$C_6$ alkyl.
6. The compound of any one of embodiments 1-4 wherein $R_2$ is methyl.
7. The compound of any one of embodiments 1-4, wherein $R_2$ is H.
8. The compound of any one of embodiments 1-7, wherein $R_3$ is H and X is absent.
9. The compound of any one of embodiments 1-7, wherein $R_3$ is halogen and X is absent.
10. The compound of any one of embodiments 1-7, wherein $R_3$ is H and X is O.
11. The compound of any one of embodiments 1-7, wherein $R_3$ is $C_1$-$C_6$ alkyl and X is O.
12. The compound of any one of embodiments 1-11, wherein $R_4$ is H and Y is absent.
13. The compound of any one of embodiments 1-11, wherein $R_4$ is H and Y is O.
14. The compound of any one of embodiments 1-11, wherein $R_4$ is halogen and Y is absent.
15. The compound of any one of embodiments 1-11, wherein $R_4$ is $C_1$-$C_6$ alkyl and Y is O.
16. The compound of any one of embodiments 1-15, wherein $R_5$ is H and Z is absent.
17. The compound of any one of embodiments 1-15, wherein $R_5$ is H and Z is O.
18. The compound of any one of embodiments 1-15, wherein $R_5$ is halogen and Z is absent.
19. The compound of any one of embodiments 1-15, wherein $R_5$ is $C_1$-$C_6$ alkyl and Z is absent.
20. The compound of any one of embodiments 1-15, wherein $R_5$ is $C_1$-$C_6$ alkyl and Z is O.
21. The compound of any one of embodiments 1-20, wherein $R_6$ is $-(C{=}O)(CR_7R_7')_n-ONO_2$.
22. The compound of any one of embodiments 1-20, wherein $R_6$ is $-(C{=}O)(CR_7R_7')_m-CH(NH_2)CH_2ONO_2$.
23. The compound of any one of embodiments 1-20, wherein $R_6$ is $-(C{=}O)(CH_2)_n-ONO_2$.
24. The compound of any one of embodiments 1-20, wherein $R_6$ is $-(C{=}O)(CH_2)_m-CH(NH_2)CH_2ONO_2$.
25. The compound of any one of embodiments 1-20, wherein $R_6$ is $-(C{=}O)(CH_2)_3-ONO_2$.
26. The compound of any one of embodiments 1-25, having the following chemical formula:

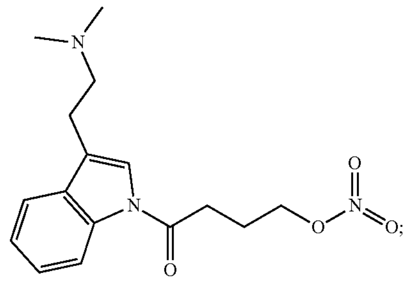 [SMILES: CN(C)CCc1cn(C(=O)CCCO[N+](=O)[O-])c2ccccc12]

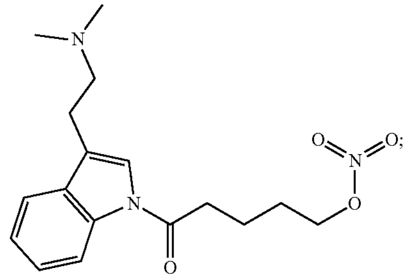

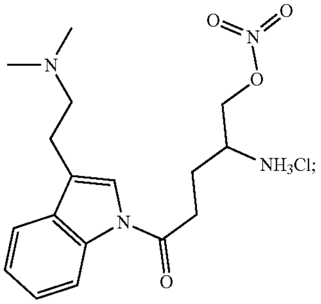

-continued
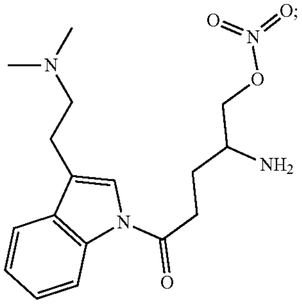
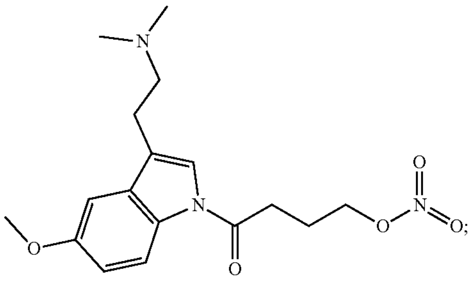
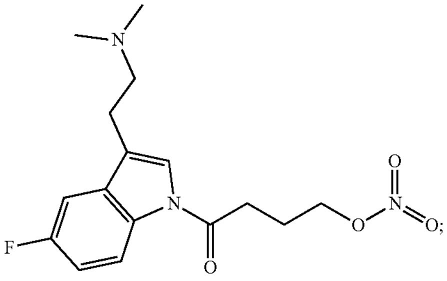
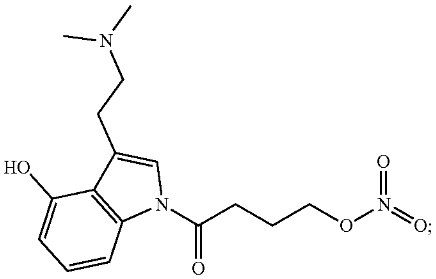
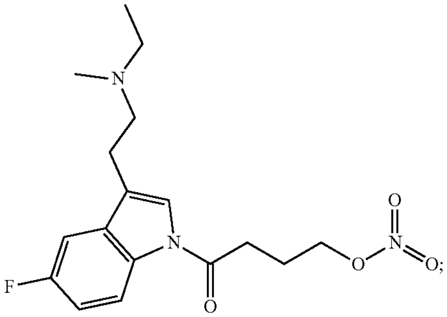 [SMILES: CCN(C)CCc1cn(C(=O)CCCO[N+](=O)[O-])c2ccc(F)cc12]
-continued
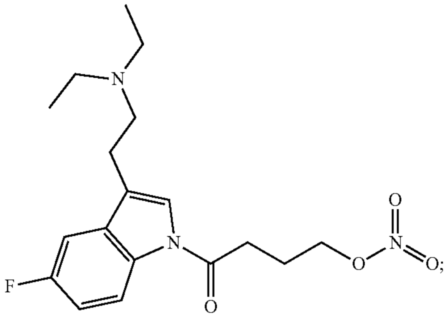
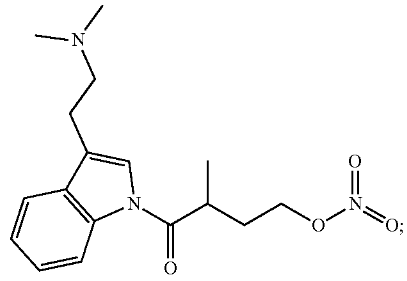
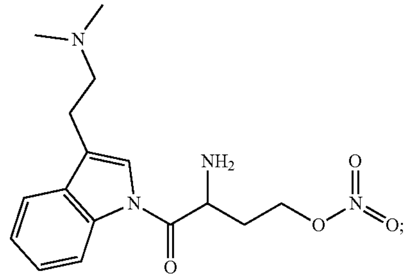
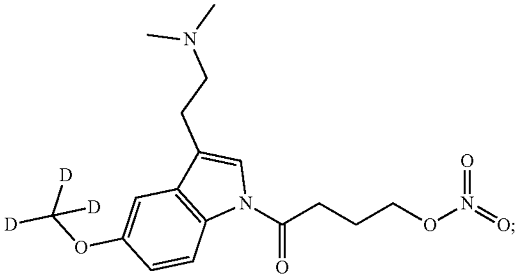
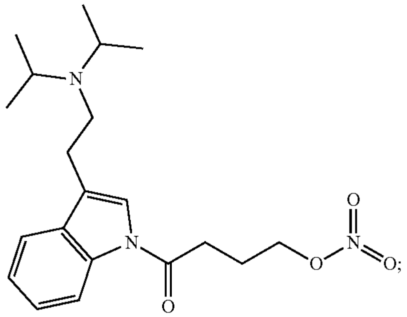
or -continued

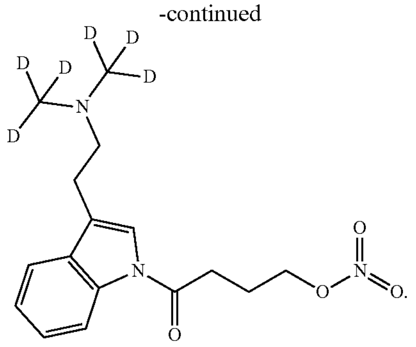

27. The compound of embodiment 26, having the following chemical formula:

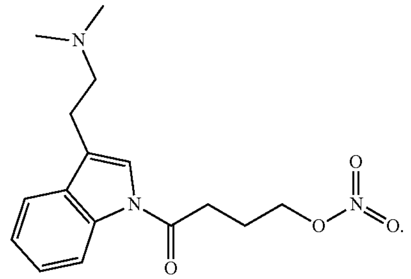 [SMILES: CN(C)CCc1cn(C(=O)CCCO[N+](=O)[O-])c2ccccc12]

28. The compound of embodiment 26, having the following chemical formula:

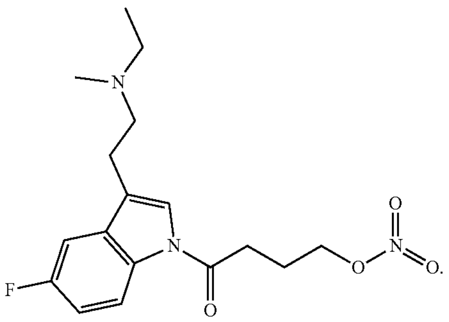 [SMILES: CCN(C)CCc1cn(C(=O)CCCO[N+](=O)[O-])c2ccc(F)cc12]

29. A pharmaceutical composition, comprising a compound of any one of embodiments 1-28 and a pharmaceutically acceptable excipient.

30. A method of treating a mental health disease or disorder, the method comprising administering a therapeutically effective amount of a compound of any one of embodiments 1-28 or pharmaceutical composition of embodiment 29.

31. A compound of Formula (I):

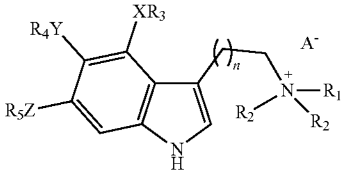

or a pharmaceutically acceptable salt thereof; wherein, $R_1$, $R_3$, $R_4$ and $R_5$ are independently H, halogen, $C_1$-$C_6$ alkyl, $—(C{=}O)(CR_7R_7')_n—ONO_2$, or $—(C{=}O)(CR_7R_7')_m—CH(NH_2)CH_2ONO_2$;

$R_2$ is $C_1$-$C_6$ alkyl;

X, Y, and Z are independently absent, H, O, S, NH and $—O—(P{=}O)OHO—$;

m is 2, 3, or 4;

each n is independently 1, 2, 3, 4 or 5; and $A^-$ is a pharmaceutically acceptable anion, wherein at least one of $R_1$, $R_3$, $R_4$ and $R_5$ are $—(C{=}O)(CR_7R_7')_n—ONO_2$ or $—(C{=}O)(CR_7R_7')_m—CH(NH_2)CH_2ONO_2$.

32. The compound of embodiment 31, wherein $R_1$ is $—(C{=}O)(CR_7R_7')_n—ONO_2$.

33. The compound of embodiment 31, wherein $R_1$ is $—(C{=}O)(CR_7R_7')_m—CH(NH_2)CH_2ONO_2$.

34. The compound of embodiment 31, wherein $R_1$ is $—(C{=}O)(CH_2)_n—ONO_2$.

35. The compound of embodiment 31, wherein $R_1$ is $—(C{=}O)(CH_2)_m—CH(NH_2)CH_2ONO_2$.

36. The compound of embodiment 31, wherein $R_1$ is $—(C{=}O)(CH_2)_3—ONO_2$.

37. The compound of embodiment 31, wherein $R_1$ is $—(C{=}O)(CH_2)_2—CH(NH_2)CH_2ONO_2$.

38. The compound of any one of embodiments 31-37, wherein $R_2$ is a $C_1$-$C_3$ alkyl.

39. The compound of any one of embodiments 31-38, wherein $R_3$ is H and X is absent.

40. The compound of any one of embodiments 31-38, wherein $R_3$ is halogen and X is absent.

41. The compound of any one of embodiments 31-38, wherein $R_3$ is H and X is O.

42. The compound of any one of embodiments 31-38, wherein $R_3$ is $C_1$-$C_6$ alkyl and X is O.

43. The compound of any one of embodiments 31-42, wherein $R_4$ is H and Y is absent.

44. The compound of any one of embodiments 31-42, wherein $R_4$ is H and Y is O.

45. The compound of any one of embodiments 31-42, wherein $R_4$ is halogen and Y is absent.

46. The compound of any one of embodiments 31-42, wherein $R_4$ is $C_1$-$C_6$ alkyl and Y is O.

47. The compound of any one of embodiments 31-46, wherein $R_5$ is H and Z is absent.

48. The compound of any one of embodiments 31-46, wherein $R_5$ is H and Z is O.

49. The compound of any one of embodiments 31-46, wherein $R_5$ is halogen and Z is absent.

50. The compound of any one of embodiments 31-46, wherein $R_5$ is $C_1$-$C_6$ alkyl and Z is O.

51. A pharmaceutical composition, comprising a compound of any one of embodiments 31-50 and a pharmaceutically acceptable excipient.

52. A method of treating a mental health disease or disorder, the method comprising administering a therapeutically effective amount of a compound of any one of embodiments 31-50 or pharmaceutical composition of embodiment 51.

EXAMPLES

Example 1: Methods of Preparing the Compounds of the Present Disclosure

Synthesis of Compound 2-1

Prodrug 2-1 was synthesized from commercially available intermediate 2-1-1 and 2-1-3 in three steps and described in the Scheme 1.

Scheme 1

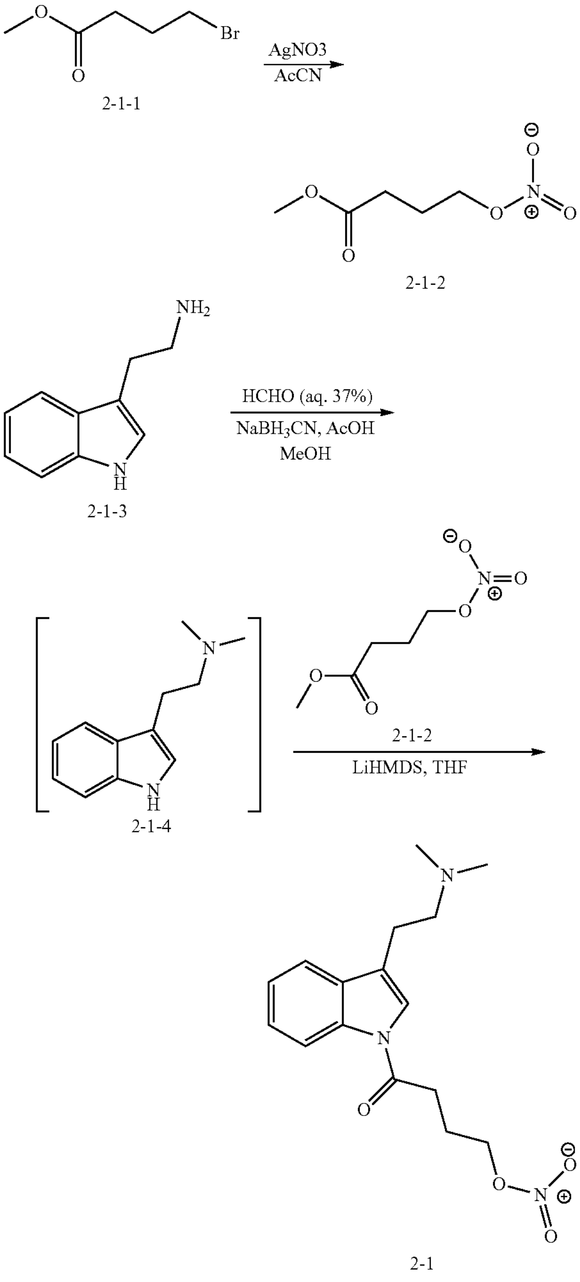

Synthesis of Intermediate 2-1-1

To a stirred solution of methyl 4-bromobutanoate, 2-1-1 (3 g, 16.5 mmol, 1.0 equiv) in acetonitrile was added $AgNO_3$ (7.0 g, 41.4 mmol, 2.5 equiv) in portions at room temperature under argon atmosphere. The resulting mixture was stirred for overnight at 80° C. under argon atmosphere. New pot could be detected by TLC. The resulting mixture was filtered, the filter cake was washed with acetonitrile (3×50 mL). The filtrate was concentrated under reduced pressure. The residue was dissolved in ethyl acetate (500 mL). The resulting mixture was washed with 2×500 mL of water. and then the resulting mixture was washed with 3×300 mL of brine. The combined organic layers dried over anhydrous $Na_2SO_4$. After filtration, the filtrate was concentrated under reduced pressure to afford methyl 4-(nitrooxy)butanoate, 2-1-2 (2.3 g, 85.08%) as a yellow oil. This crude product was used directly for the next step without further purification.

Synthesis of intermediate 2-1-4 and final Product 1-(3-(2-(dimethylamino)ethyl)-1H-indol-1-yl)-4-(nitrooxy)butanoate (2-1)

To a stirred solution of tryptamine (200 mg, 1.2 mmol, 1.0 equiv) and $NaBH_3CN$ (235.3 mg, 3.7 mmol, 3.0 equiv), AcOH (0.2 mL) in MeOH was added formaldehyde solution (187.4 mg, 6.24 mmol, 5.0 equiv) dropwise at 0° C. under argon atmosphere. The resulting mixture was stirred for overnight at room temperature under argon atmosphere. Desired product could be detected by LCMS. The resulting mixture was filtered, the filter cake was washed with MeOH (3×10 mL). The filtrate was concentrated under reduced pressure. The residue was purified by silica gel column chromatography, eluted with PE/EA (1:1) to afford intermediate as a yellow solid. To a stirred solution of intermediate and methyl 4-(nitrooxy)butanoate (610.8 mg, 3.7 mmol, 3.0 equiv) in THF was added LiHMDS (313.3 mg, 1.8 mmol, 1.5 equiv) in THF dropwise at 0° C. under argon atmosphere. The resulting mixture was stirred for 1 h at 0° C. under argon atmosphere. Desired product could be detected by LCMS. The reaction was quenched with MeOH at 0° C. The resulting mixture was concentrated under vacuum. The residue was purified by reversed-phase flash chromatography with the following conditions: column, $C_{18}$ silica gel; mobile phase, MeCN in Water (0.1% FA), 5% to 80% gradient in 40 min; detector, UV 254 nm. to afford 25 mg of 1-(3-(2-(dimethylamino)ethyl)-1H-indol-1-yl)-4-(nitrooxy) butanoate (2-1) as a white solid. LCMS of 2-1: $[M+H]^+$ 320.10

HNMR-2-1: (400 MHz, DMSO-d6) δ 8.07 (d, J=8.2 Hz, 1H), 7.62 (d, J=7.7 Hz, 1H), 7.52 (s, 1H), 7.36-7.25 (m, 2H), 4.79 (t, J=6.7 Hz, 2H), 4.47 (t, J=6.0 Hz, 2H), 2.80 (t, J=7.5 Hz, 2H), 2.57-2.40 (m, 4H), 2.22 (s, 6H).

What is claimed:

1. A method of treating a mental health disease or disorder, the method comprising administering to a subject in need thereof a compound of Formula (II):

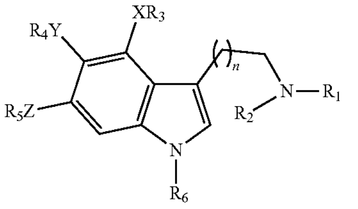

or a pharmaceutically acceptable salt thereof; wherein, $R_3$, $R_4$, and $R_5$ are independently H, halogen, or $C_1$-$C_6$ alkyl;

$R_6$ is —(C═O)$(CR_7R_7')_n$—$ONO_2$, or —(C═O)$(CR_7R_7')_m$—$CH(NH_2)CH_2ONO_2$;

$R_1$ and $R_2$ are each independently H or $C_1$-$C_6$ alkyl; and $R_7$ and $R_7'$ are independently H, halogen, or $C_1$-$C_6$ alkyl;

X, Y, and Z are independently absent or O;

m is 2, 3, or 4; and each n is independently 1, 2, 3, 4 or 5.

2. The method of claim 1, wherein $R_1$ is $C_1$-$C_6$ alkyl.

3. The method of claim 1, wherein $R_1$ is methyl.

4. The method of claim 1, wherein $R_1$ is H.

5. The method of claim 1, wherein $R_2$ is $C_1$-$C_6$ alkyl.

6. The method of claim 1, wherein $R_2$ is methyl.

7. The method of claim 1, wherein $R_2$ is H.

8. The method of claim 1, wherein $R_3$ is H and X is absent.

9. The method of claim 1, wherein $R_3$ is halogen and X is absent.

10. The method of claim 1, wherein $R_3$ is H and X is O.

11. The method of claim 1, wherein $R_3$ is $C_1$-$C_6$ alkyl and X is O.

12. The method of claim 1, wherein $R_4$ is H and Y is absent.

13. The method of claim 1, wherein $R_4$ is H and Y is O.

14. The method of claim 1, wherein $R_4$ is halogen and Y is absent.

15. The method of claim 1, wherein $R_4$ is $C_1$-$C_6$ alkyl and Y is O.

16. The method of claim 1, wherein $R_5$ is H and Z is absent.

17. The method of claim 1, wherein $R_5$ is H and Z is O.

18. The method of claim 1, wherein $R_5$ is halogen and Z is absent.

19. The method of claim 1, wherein $R_5$ is $C_1$-$C_6$ alkyl and Z is absent.

20. The method of claim 1, wherein $R_5$ is $C_1$-$C_6$ alkyl and Z is O.

21. The method of claim 1, wherein $R_6$ is $-(C{=}O)(CR_7R_7')_n-ONO_2$.

22. The method of claim 1, wherein $R_6$ is $-(C{=}O)(CR_7R_7')_m-CH(NH_2)CH_2ONO_2$.

23. The method of claim 1, wherein $R_6$ is $-(C{=}O)(CH_2)_n-ONO_2$.

24. The method of claim 1, wherein $R_6$ is $-(C{=}O)(CH_2)_m-CH(NH_2)CH_2ONO_2$.

25. The method of claim 1, wherein $R_6$ is $-(C{=}O)(CH_2)_3-ONO_2$.

26. The method of claim 1, wherein the compound has the following chemical formula:

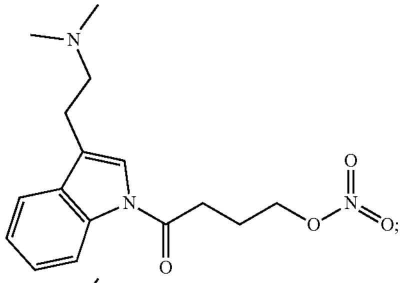

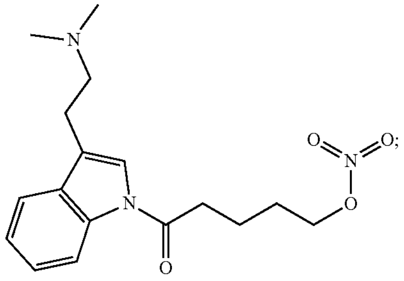

-continued

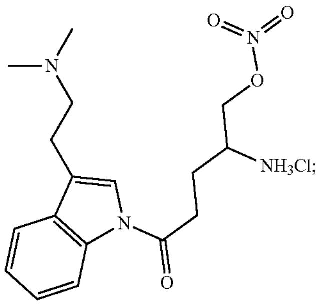

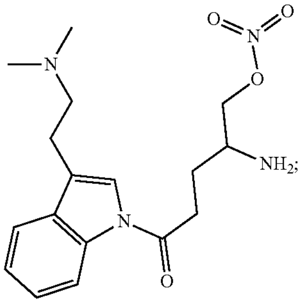

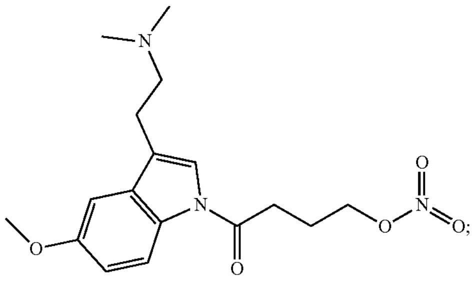

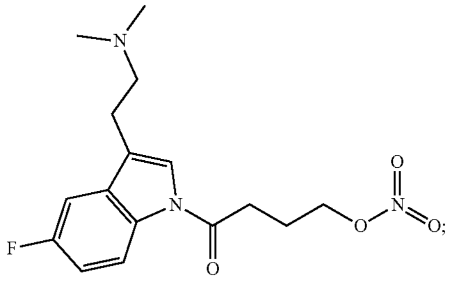

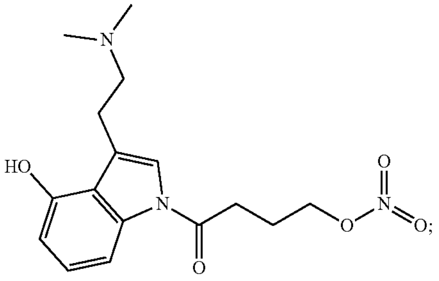

-continued

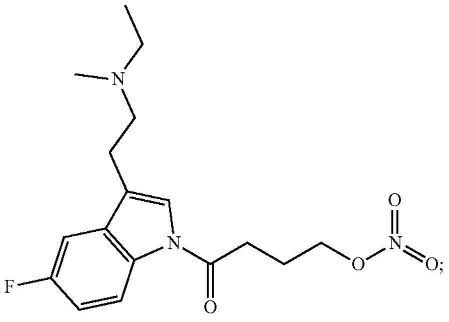

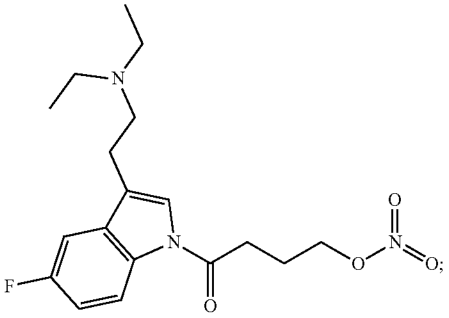

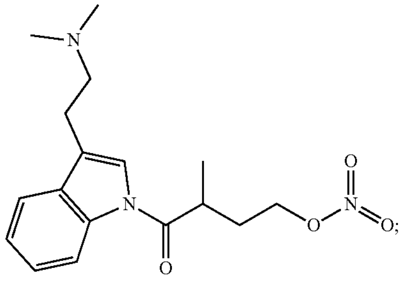

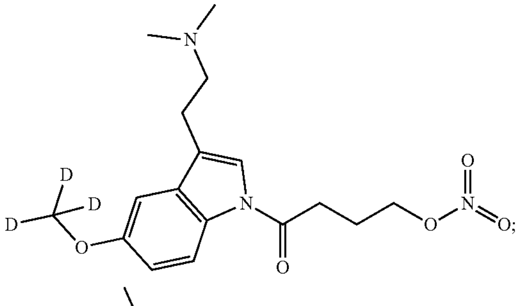

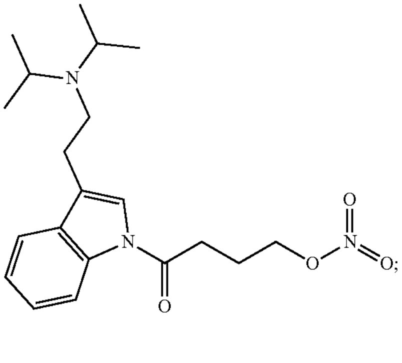

or

-continued

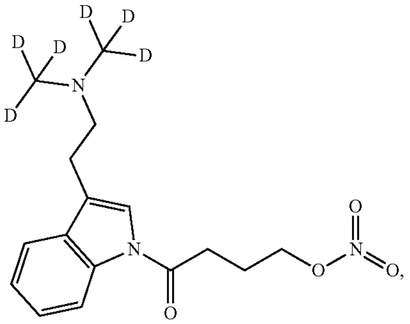

or a pharmaceutically acceptable salt thereof.

27. The method of claim 26, wherein the compound has the following chemical formula:

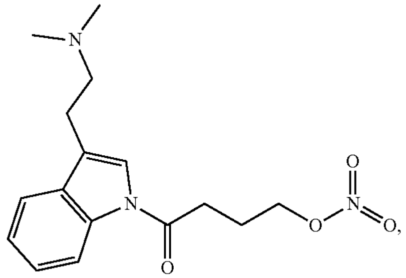

or a pharmaceutically acceptable salt thereof.

28. The method of claim 26, wherein the compound has the following chemical formula:

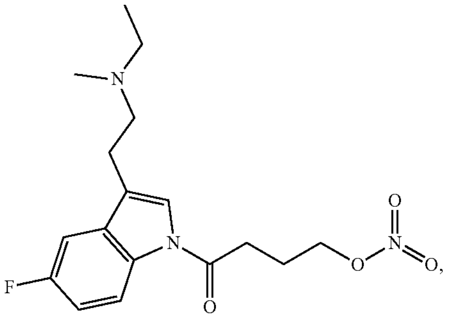

or a pharmaceutically acceptable salt thereof.

29. The method of claim 1. wherein the compound is administered in a pharmaceutical composition comprising a pharmaceutically acceptable excipient.

30. A method of treating a mental health disease or disorder, the method comprising administering a therapeutically effective amount of a compound having the following formula:

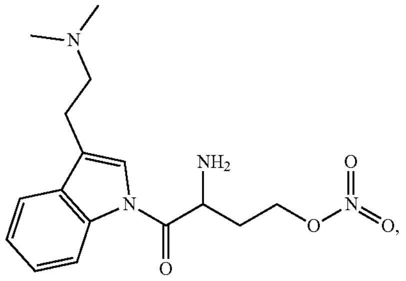 [SMILES: CN(C)CCc1cn(C(=O)C(N)CCO[N+](=O)[O-])c2ccccc12]

or a pharmaceutically acceptable salt thereof.

31. The method of claim 1, wherein the mental health disease or disorder the mental is selected from the group consisting of major depressive disorder, treatment resistant depression, a substance use disorder, an eating disorder, a compulsive disorder, an anxiety disorder, and rumination.

32. The method of claim 31, wherein the eating disorder is anorexia nervosa, bulimia nervosa, or binge eating disorder.

33. The method of claim 30, wherein the mental health disease or disorder the mental is selected from the group consisting of major depressive disorder, treatment resistant depression, a substance use disorder, an eating disorder, a compulsive disorder, an anxiety disorder, and rumination.

34. The method of claim 33, wherein the eating disorder is anorexia nervosa, bulimia nervosa, or binge eating disorder.

* * * * *